(12) United States Patent
Lippert et al.

(10) Patent No.: US 11,951,267 B2
(45) Date of Patent: Apr. 9, 2024

(54) GUIDEWIRE DEVICES HAVING SHAPEABLE TIPS AND BYPASS CUTS

(71) Applicant: SCIENTIA VASCULAR, INC., West Valley City, UT (US)

(72) Inventors: John A Lippert, Park City, UT (US); Edward J. Snyder, Park City, UT (US); Clark C. Davis, Holladay, UT (US)

(73) Assignee: Scientia Vascular, Inc., West Valley City, UT (US)

( * ) Notice: Subject to any disclaimer, the term of this patent is extended or adjusted under 35 U.S.C. 154(b) by 300 days.

(21) Appl. No.: 17/335,314

(22) Filed: Jun. 1, 2021

(65) Prior Publication Data

US 2021/0283380 A1   Sep. 16, 2021

Related U.S. Application Data

(60) Division of application No. 15/917,255, filed on Mar. 9, 2018, now Pat. No. 11,052,228, which is a
(Continued)

(51) Int. Cl.
*A61M 25/09* (2006.01)

(52) U.S. Cl.
CPC ... *A61M 25/09* (2013.01); *A61M 2025/09083* (2013.01); *A61M 2025/09091* (2013.01);
(Continued)

(58) Field of Classification Search
CPC ........ A61M 25/09; A61M 2025/09083; A61M 2025/09133; A61M 2025/0915; A61M 2025/08175
See application file for complete search history.

(56) References Cited

U.S. PATENT DOCUMENTS 2,022,065 A   11/1935   Wappler
2,187,299 A   1/1940   Otto
(Continued)

FOREIGN PATENT DOCUMENTS

AU   07230/40 B2   8/2000
AU   733966 B2   5/2001
(Continued)

OTHER PUBLICATIONS

Final Office Action received for U.S. Appl. No. 15/848,878, dated Sep. 22, 2021, 12 pages.
(Continued)

*Primary Examiner* — Daniel L Cerioni
(74) *Attorney, Agent, or Firm* — WORKMAN NYDEGGER

(57) ABSTRACT

The present disclosure relates to guidewire devices having shapeable tips and effective torquability. A guidewire device includes a core having a proximal section and a tapered distal section. A tube structure is coupled to the core such that the tapered distal section extends into the tube structure. The tube structure includes a plurality of bypass cuts formed tangentially within the tube structure to increase the flexibility of the tube structure and to reduce the tendency of resilient forces from the tube structure to disrupt a shaped distal tip of the guidewire device.

19 Claims, 7 Drawing Sheets

Related U.S. Application Data continuation-in-part of application No. 15/606,607, filed on May 26, 2017, now Pat. No. 11,207,502.

(60) Provisional application No. 62/363,760, filed on Jul. 18, 2016.

(52) U.S. Cl.
CPC ............ *A61M 2025/09133* (2013.01); *A61M 2025/0915* (2013.01); *A61M 2025/09166* (2013.01); *A61M 2025/09175* (2013.01)

(56) References Cited

U.S. PATENT DOCUMENTS

| | | | |
|---|---|---|---|
| 3,183,702 A | 5/1965 | Zittell |
| 3,572,334 A | 3/1971 | Petterson |
| 3,612,058 A | 10/1971 | Ackerman |
| 3,709,271 A | 1/1973 | Flory |
| 3,782,233 A | 1/1974 | Helm |
| 3,920,058 A | 11/1975 | Walker |
| 4,163,406 A | 8/1979 | Crawford |
| 4,239,069 A | 12/1980 | Zimmerman |
| 4,416,312 A | 11/1983 | Oestberg |
| 4,688,540 A | 8/1987 | Ono |
| 4,719,924 A | 1/1988 | Crittenden et al. |
| 4,801,297 A | 1/1989 | Mueller |
| 4,846,186 A | 7/1989 | Box et al. |
| 4,895,168 A | 1/1990 | Machek |
| 4,989,608 A | 2/1991 | Ratner |
| 5,047,045 A | 9/1991 | Arney et al. |
| 5,069,217 A | 12/1991 | Fleischhacker, Jr. |
| 5,084,022 A | 1/1992 | Claude |
| 5,095,915 A | 3/1992 | Engelson |
| 5,102,390 A | 4/1992 | Crittenden et al. |
| 5,144,959 A | 9/1992 | Gambale et al. |
| 5,147,317 A | 9/1992 | Shank et al. |
| 5,154,725 A | 10/1992 | Leopold |
| 5,174,302 A | 12/1992 | Palmer |
| 5,315,996 A | 5/1994 | Lundquist |
| 5,326,374 A | 7/1994 | Ilbawi et al. |
| 5,345,945 A | 9/1994 | Hodgson et al. |
| 5,372,587 A | 12/1994 | Hammerslag et al. |
| 5,382,259 A | 1/1995 | Phelps et al. |
| 5,385,152 A | 1/1995 | Abele et al. |
| 5,437,288 A | 8/1995 | Schwartz et al. |
| 5,441,483 A | 8/1995 | Avitall |
| 5,506,682 A | 4/1996 | Pryor |
| 5,507,751 A | 4/1996 | Goode et al. |
| 5,551,444 A | 9/1996 | Finlayson |
| 5,554,114 A | 9/1996 | Wallace et al. |
| 5,569,218 A | 10/1996 | Berg |
| 5,573,520 A | 11/1996 | Schwartz et al. |
| 5,573,867 A | 11/1996 | Zafred et al. |
| 5,659,205 A | 8/1997 | Weisser |
| 5,673,707 A | 10/1997 | Chandrasekaran |
| 5,676,659 A | 10/1997 | McGurk |
| 5,685,568 A | 11/1997 | Pirrello |
| 5,685,868 A | 11/1997 | Lundquist |
| 5,690,120 A | 11/1997 | Jacobsen et al. |
| 5,706,826 A | 1/1998 | Schwager |
| 5,741,429 A | 4/1998 | Donadio et al. |
| 5,746,701 A | 5/1998 | Noone |
| 5,792,154 A | 8/1998 | Doan et al. |
| 5,800,454 A | 9/1998 | Jacobsen et al. |
| 5,833,631 A | 11/1998 | Nguyen |
| 5,833,632 A | 11/1998 | Jacobsen et al. |
| 5,842,461 A | 12/1998 | Azuma |
| 5,860,963 A | 1/1999 | Azam et al. |
| 5,876,356 A | 3/1999 | Viera et al. |
| 5,911,715 A | 6/1999 | Berg et al. |
| 5,911,717 A | 6/1999 | Jacobsen et al. |
| 5,916,194 A | 6/1999 | Jacobsen et al. |
| 5,931,830 A | 8/1999 | Jacobsen et al. |
| 5,954,672 A | 9/1999 | Schwager |
| 6,004,279 A | 12/1999 | Crowley et al. |
| 6,014,919 A | 1/2000 | Jacobsen |
| 6,017,319 A | 1/2000 | Jacobsen et al. |
| 6,022,343 A | 2/2000 | Johnson et al. |
| 6,022,369 A | 2/2000 | Jacobsen et al. |
| 6,027,863 A | 2/2000 | Donadio, III |
| 6,033,288 A | 3/2000 | Weisshaus et al. |
| 6,033,394 A | 3/2000 | Vidlund et al. |
| 6,056,702 A | 5/2000 | Lorenzo |
| 6,063,101 A | 5/2000 | Jacobsen et al. |
| 6,110,164 A | 8/2000 | Vidlund |
| 6,132,389 A | 10/2000 | Cornish et al. |
| 6,139,511 A | 10/2000 | Huter et al. |
| 6,168,570 B1 | 1/2001 | Ferrera |
| 6,179,828 B1 | 1/2001 | Mottola et al. |
| 6,183,410 B1 | 2/2001 | Jacobsen et al. |
| 6,183,420 B1 | 2/2001 | Douk et al. |
| 6,214,042 B1 | 4/2001 | Jacobsen et al. |
| 6,228,073 B1 | 5/2001 | Noone et al. |
| 6,245,030 B1 | 6/2001 | Dubois et al. |
| 6,251,086 B1 | 6/2001 | Cornelius et al. |
| 6,260,458 B1 | 7/2001 | Jacobsen et al. |
| 6,261,246 B1 | 7/2001 | Pantages et al. |
| 6,273,881 B1 | 8/2001 | Kiemeneij |
| 6,302,870 B1 | 10/2001 | Jacobsen et al. |
| 6,306,105 B1 | 10/2001 | Rooney et al. |
| 6,346,091 B1 | 2/2002 | Jacobsen et al. |
| 6,356,791 B1 | 3/2002 | Westlund et al. |
| 6,402,706 B2 | 6/2002 | Richardson et al. |
| 6,428,489 B1 | 8/2002 | Jacobsen et al. |
| 6,431,039 B1 | 8/2002 | Jacobsen et al. |
| 6,436,056 B1 | 8/2002 | Wang et al. |
| 6,440,088 B1 | 8/2002 | Jacobsen et al. |
| 6,458,867 B1 | 10/2002 | Wang et al. |
| 6,464,651 B1 | 10/2002 | Hiejima et al. |
| 6,492,615 B1 | 12/2002 | Flanagan |
| 6,494,894 B2 | 12/2002 | Mirarchi |
| 6,527,732 B1 | 3/2003 | Strauss et al. |
| 6,527,746 B1 | 3/2003 | Oslund et al. |
| 6,553,880 B2 | 4/2003 | Jacobsen et al. |
| 6,554,820 B1 | 4/2003 | Wendlandt et al. |
| 6,558,355 B1 | 5/2003 | Metzger et al. |
| 6,579,246 B2 | 6/2003 | Jacobsen et al. |
| 6,602,207 B1 | 8/2003 | Mam et al. |
| 6,606,985 B2 | 8/2003 | Negishi |
| 6,610,046 B1 | 8/2003 | Usami et al. |
| 6,627,724 B2 | 9/2003 | Meijs et al. |
| 6,652,508 B2 | 11/2003 | Griffin et al. |
| 6,671,560 B2 | 12/2003 | Westlund et al. |
| 6,766,720 B1 | 7/2004 | Jacobsen et al. |
| 6,805,676 B2 | 10/2004 | Klint |
| 6,866,642 B2 | 3/2005 | Kellerman et al. |
| RE39,018 E | 3/2006 | Azuma et al. |
| 7,024,885 B2 | 4/2006 | Villalobos |
| 7,097,624 B2 | 8/2006 | Campion et al. |
| 7,110,910 B1 | 9/2006 | Deffenbaugh et al. |
| 7,128,718 B2 | 10/2006 | Hojeibane et al. |
| 7,182,735 B2 | 2/2007 | Shireman et al. |
| 7,276,062 B2 | 10/2007 | McDaniel et al. |
| 7,338,345 B2 | 3/2008 | Fujinami |
| 7,421,929 B2 | 9/2008 | French |
| 7,494,474 B2 | 2/2009 | Richardson et al. |
| 7,507,246 B2 | 3/2009 | McGuckin et al. |
| 7,621,880 B2 | 11/2009 | Ryan et al. |
| 7,637,875 B2 | 12/2009 | Itou |
| 7,641,622 B2 | 1/2010 | Satou et al. |
| 7,670,302 B2 | 3/2010 | Griffin et al. |
| 7,699,792 B2 | 4/2010 | Hofmann et al. |
| 7,722,545 B2 | 5/2010 | Bertsch |
| 7,722,552 B2 | 5/2010 | Aimi et al. |
| 7,744,545 B2 | 6/2010 | Aimi et al. |
| 7,747,314 B2 | 6/2010 | Parins et al. |
| 7,753,859 B2 | 7/2010 | Kinoshita et al. |
| 7,766,896 B2 | 8/2010 | Kornkven et al. |
| 7,769,839 B2 | 8/2010 | Boivie et al. |
| 7,785,273 B2 | 8/2010 | Eskuri |
| 7,789,839 B2 | 9/2010 | Lupton |
| 7,806,837 B2 | 10/2010 | Rasmussen et al. |
| 7,878,984 B2 | 2/2011 | Jacobsen et al. |

(56) References Cited

U.S. PATENT DOCUMENTS

| | | |
|---|---|---|
| 7,883,474 B1 | 2/2011 | Mirigian et al. |
| 7,914,467 B2 | 3/2011 | Layman et al. |
| 7,942,832 B2 | 5/2011 | Kanuka et al. |
| 7,989,042 B2 | 8/2011 | Obara et al. |
| 8,043,314 B2 | 10/2011 | Noriega et al. |
| 8,048,004 B2 | 11/2011 | Davis et al. |
| 8,105,246 B2 | 1/2012 | Voeller et al. |
| 8,128,579 B2 | 3/2012 | Chen et al. |
| 8,128,580 B2 | 3/2012 | Fujimagari et al. |
| 8,137,293 B2 | 3/2012 | Zhou et al. |
| 8,167,821 B2 | 5/2012 | Sharrow |
| 8,257,279 B2 | 9/2012 | Jacobsen |
| 8,292,828 B2 | 10/2012 | Bernhard |
| 8,357,140 B2 | 1/2013 | Majercak et al. |
| 8,376,961 B2 | 2/2013 | Layman et al. |
| 8,377,056 B2 | 2/2013 | Oyola et al. |
| 8,409,114 B2 | 4/2013 | Parins |
| 8,409,169 B1 | 4/2013 | Moss |
| 8,444,577 B2 | 5/2013 | Bunch et al. |
| 8,454,535 B2 | 6/2013 | Majercak et al. |
| 8,460,213 B2 | 6/2013 | Northrop |
| 8,468,919 B2 | 6/2013 | Christian et al. |
| 8,500,658 B2 | 8/2013 | Boyle et al. |
| 8,517,959 B2 | 8/2013 | Kurosawa et al. |
| 8,535,243 B2 | 9/2013 | Shireman |
| 8,540,648 B2 | 9/2013 | Uihlein |
| 8,551,020 B2 | 10/2013 | Chen et al. |
| 8,551,021 B2 | 10/2013 | Voeller et al. |
| 8,622,931 B2 | 1/2014 | Teague et al. |
| 8,622,933 B2 | 1/2014 | Maki et al. |
| 8,728,075 B2 | 5/2014 | Wu et al. |
| 8,758,269 B2 | 6/2014 | Miyata et al. |
| 8,795,202 B2 | 8/2014 | Northrop et al. |
| 8,795,254 B2 | 8/2014 | Layman et al. |
| 8,821,477 B2 | 9/2014 | Northrop et al. |
| 8,870,790 B2 | 10/2014 | Davis et al. |
| 8,900,163 B2 | 12/2014 | Jacobsen et al. |
| 8,915,865 B2 | 12/2014 | Jacobsen et al. |
| 8,932,235 B2 | 1/2015 | Jacobsen et al. |
| 8,936,558 B2 | 1/2015 | Jacobsen et al. |
| 8,939,916 B2 | 1/2015 | Jacobsen et al. |
| 8,956,310 B2 | 2/2015 | Miyata et al. |
| 9,067,332 B2 | 6/2015 | Lippert et al. |
| 9,067,333 B2 | 6/2015 | Lippert et al. |
| 9,072,873 B2 | 7/2015 | Lippert et al. |
| 9,072,874 B2 | 7/2015 | Northrop et al. |
| 9,364,589 B2 | 6/2016 | Cage et al. |
| 9,550,013 B2 | 1/2017 | Kawasaki |
| 9,616,195 B2 | 4/2017 | Lippert et al. |
| 9,623,212 B2 | 4/2017 | Tano et al. |
| 9,662,798 B2 | 5/2017 | Christian et al. |
| 9,700,702 B2 | 7/2017 | Tano et al. |
| 9,848,882 B2 | 12/2017 | Lippert |
| 9,950,137 B2 | 4/2018 | Lippert et al. |
| 10,252,024 B2 | 4/2019 | Northrop |
| 10,363,389 B2 | 7/2019 | Lippert et al. |
| 10,639,456 B2 | 5/2020 | Peralta |
| 11,052,228 B2 | 7/2021 | Lippert et al. |
| 2001/0009980 A1 | 7/2001 | Richardson et al. |
| 2002/0013540 A1 | 1/2002 | Jacobsen et al. |
| 2002/0019599 A1 | 2/2002 | Rooney et al. |
| 2002/0049392 A1 | 4/2002 | Demello |
| 2002/0062524 A1 | 5/2002 | Vogland et al. |
| 2002/0068912 A1 | 6/2002 | Merdan |
| 2002/0078808 A1 | 6/2002 | Jacobsen et al. |
| 2002/0082524 A1 | 6/2002 | Anderson et al. |
| 2003/0009208 A1 | 1/2003 | Snyder et al. |
| 2003/0023190 A1 | 1/2003 | Cox |
| 2003/0060732 A1 | 3/2003 | Jacobsen et al. |
| 2003/0069521 A1 | 4/2003 | Reynolds et al. |
| 2003/0069522 A1 | 4/2003 | Jacobsen et al. |
| 2003/0093059 A1 | 5/2003 | Griffin et al. |
| 2003/0125641 A1 | 7/2003 | Jafari et al. |
| 2004/0039371 A1 | 2/2004 | Tockman et al. |
| 2004/0054349 A1 | 3/2004 | Brightbill |
| 2004/0087933 A1 | 5/2004 | Lee et al. |
| 2004/0093060 A1 | 5/2004 | Seguin et al. |
| 2004/0102719 A1 | 5/2004 | Keith et al. |
| 2004/0102720 A1 | 5/2004 | Kellerman et al. |
| 2004/0111044 A1 | 6/2004 | Davis et al. |
| 2004/0122340 A1 | 6/2004 | Vrba et al. |
| 2004/0167437 A1 | 8/2004 | Sharrow et al. |
| 2004/0167440 A1 | 8/2004 | Sharrow |
| 2004/0171996 A1 | 9/2004 | Kiemeneij |
| 2004/0181174 A2 | 9/2004 | Davis et al. |
| 2004/0186485 A1 | 9/2004 | Kear |
| 2004/0193140 A1 | 9/2004 | Griffin et al. |
| 2004/0225292 A1 | 11/2004 | Sasso et al. |
| 2004/0254450 A1 | 12/2004 | Griffin et al. |
| 2005/0054953 A1 | 3/2005 | Ryan et al. |
| 2005/0065456 A1 | 3/2005 | Eskuri |
| 2005/0124976 A1 | 6/2005 | Devens et al. |
| 2005/0216049 A1 | 9/2005 | Jones et al. |
| 2005/0274384 A1 | 12/2005 | Tran et al. |
| 2006/0006649 A1 | 1/2006 | Galdonik et al. |
| 2006/0041186 A1 | 2/2006 | Vancaillie |
| 2006/0074442 A1 | 4/2006 | Noriega et al. |
| 2006/0089618 A1 | 4/2006 | McFerran et al. |
| 2006/0112802 A1 | 6/2006 | Fujinami |
| 2006/0121218 A1 | 6/2006 | Obara et al. |
| 2006/0189896 A1 | 8/2006 | Davis et al. |
| 2006/0241519 A1 | 10/2006 | Hojeibane et al. |
| 2006/0247661 A1 | 11/2006 | Richards et al. |
| 2006/0262474 A1 | 11/2006 | Chen et al. |
| 2007/0010786 A1 | 1/2007 | Casey et al. |
| 2007/0055302 A1 | 3/2007 | Henry et al. |
| 2007/0100285 A1 | 5/2007 | Griffin et al. |
| 2007/0112331 A1 | 5/2007 | Weber et al. |
| 2007/0135763 A1 | 6/2007 | Musbach et al. |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0221230 A1 | 9/2007 | Thompson et al. |
| 2007/0233039 A1 | 10/2007 | Mitelberg |
| 2007/0250036 A1 | 10/2007 | Volk et al. |
| 2007/0282270 A1 | 12/2007 | Mathews et al. |
| 2007/0287955 A1 | 12/2007 | Layman et al. |
| 2008/0021347 A1 | 1/2008 | Jacobsen et al. |
| 2008/0021401 A1 | 1/2008 | Jacobsen et al. |
| 2008/0021404 A1 | 1/2008 | Jacobsen et al. |
| 2008/0021406 A1 | 1/2008 | Jacobsen et al. |
| 2008/0064989 A1 | 3/2008 | Chen et al. |
| 2008/0077049 A1 | 3/2008 | Hirshman |
| 2008/0086854 A1 | 4/2008 | Boyd et al. |
| 2008/0097246 A1 | 4/2008 | Stafford |
| 2008/0097247 A1 | 4/2008 | Eskuri |
| 2008/0097248 A1 | 4/2008 | Munoz et al. |
| 2008/0119869 A1 | 5/2008 | Teague et al. |
| 2008/0122226 A1 | 5/2008 | Madison |
| 2008/0125674 A1 | 5/2008 | Bilecen et al. |
| 2008/0147170 A1 | 6/2008 | Vrba |
| 2008/0188298 A1 | 8/2008 | Seelig et al. |
| 2008/0188928 A1 | 8/2008 | Salahieh et al. |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu et al. |
| 2009/0036832 A1 | 2/2009 | Skujins et al. |
| 2009/0036833 A1 | 2/2009 | Parins |
| 2009/0043283 A1 | 2/2009 | Turnlund et al. |
| 2009/0043372 A1 | 2/2009 | Northrop et al. |
| 2009/0118675 A1 | 5/2009 | Czyscon et al. |
| 2009/0118704 A1 | 5/2009 | Sharrow et al. |
| 2009/0177119 A1 | 7/2009 | Heidner et al. |
| 2009/0177185 A1 | 7/2009 | Northrop |
| 2009/0254000 A1 | 10/2009 | Ayman et al. |
| 2009/0292225 A1 | 11/2009 | Chen et al. |
| 2009/0318892 A1 | 12/2009 | Aboytes et al. |
| 2010/0063479 A1 | 3/2010 | Merdan et al. |
| 2010/0069882 A1 | 3/2010 | Jennings et al. |
| 2010/0114017 A1 | 5/2010 | Lenker et al. |
| 2010/0114302 A1 | 5/2010 | Tzafriri et al. |
| 2010/0139465 A1 | 6/2010 | Christian et al. |
| 2010/0145308 A1 | 6/2010 | Layman et al. |

(56) References Cited

U.S. PATENT DOCUMENTS

| | | |
|---|---|---|
| 2010/0228150 A1 | 9/2010 | Zimmerman et al. |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0318066 A1 | 12/2010 | Miyata et al. |
| 2011/0011226 A1 | 1/2011 | Tsurusawa et al. |
| 2011/0022003 A1 | 1/2011 | Tekulve |
| 2011/0160680 A1 | 6/2011 | Cage et al. |
| 2011/0245807 A1 | 10/2011 | Sakata et al. |
| 2011/0245808 A1 | 10/2011 | Voeller et al. |
| 2011/0251519 A1 | 10/2011 | Romoscanu |
| 2011/0313417 A1 | 12/2011 | De et al. |
| 2012/0046575 A1 | 2/2012 | Brown |
| 2012/0065623 A1 | 3/2012 | Nelson et al. |
| 2012/0158034 A1 | 6/2012 | Wilson et al. |
| 2012/0209073 A1 | 8/2012 | Mcweeney et al. |
| 2012/0239074 A1 | 9/2012 | Aboytes et al. |
| 2012/0271397 A1 | 10/2012 | Muzslay et al. |
| 2012/0289938 A1 | 11/2012 | Northrop et al. |
| 2013/0018359 A1 | 1/2013 | Coyle |
| 2013/0096553 A1 | 4/2013 | Hill et al. |
| 2013/0110000 A1 | 5/2013 | Tully et al. |
| 2013/0131642 A1 | 5/2013 | Miyata et al. |
| 2013/0144267 A1 | 6/2013 | Chan et al. |
| 2013/0184703 A1 | 7/2013 | Shireman et al. |
| 2013/0226033 A1 | 8/2013 | Eskuri |
| 2013/0255456 A1 | 10/2013 | Christian et al. |
| 2014/0012281 A1 | 1/2014 | Wang et al. |
| 2014/0031719 A1 | 1/2014 | Kanazawa |
| 2014/0058324 A1 | 2/2014 | Salahieh et al. |
| 2014/0094787 A1 | 4/2014 | Reynolds |
| 2014/0187983 A1 | 7/2014 | Anderson |
| 2014/0257363 A1 | 9/2014 | Lippert |
| 2014/0276109 A1 | 9/2014 | Gregorich |
| 2014/0276787 A1 | 9/2014 | Wang et al. |
| 2014/0279109 A1 | 9/2014 | Vasquez et al. |
| 2014/0309657 A1 | 10/2014 | Ben-Ami |
| 2014/0336620 A1 | 11/2014 | Ayman et al. |
| 2015/0011834 A1 | 1/2015 | Ayala et al. |
| 2015/0011964 A1 | 1/2015 | Abner et al. |
| 2015/0057639 A1 | 2/2015 | Storbeck et al. |
| 2015/0190614 A1 | 7/2015 | Uihlein |
| 2015/0190615 A1 | 7/2015 | Shaltis |
| 2015/0216533 A1 | 8/2015 | Gray et al. |
| 2015/0238734 A1 | 8/2015 | Kanazawa |
| 2015/0290432 A1 | 10/2015 | Mathews et al. |
| 2015/0297863 A1 | 10/2015 | Hannon et al. |
| 2015/0305710 A1 | 10/2015 | Stigall et al. |
| 2015/0306355 A1 | 10/2015 | Idstrom |
| 2016/0001048 A1 | 1/2016 | Koike |
| 2016/0008585 A1 | 1/2016 | Tano |
| 2016/0045101 A1 | 2/2016 | Nakatate et al. |
| 2016/0058382 A1* | 3/2016 | Burkett .............. A61B 18/1492 156/60 |
| 2016/0089128 A1 | 3/2016 | Weber et al. |
| 2016/0113793 A1 | 4/2016 | Nishigishi |
| 2016/0135827 A1 | 5/2016 | Elsesser et al. |
| 2016/0199620 A1 | 7/2016 | Pokorney et al. |
| 2016/0235337 A1 | 8/2016 | Govari et al. |
| 2016/0361520 A1 | 12/2016 | Braun |
| 2016/0367788 A1 | 12/2016 | Jimenez et al. |
| 2016/0375226 A1 | 12/2016 | Nabeshima et al. |
| 2017/0047740 A1 | 2/2017 | Narla |
| 2017/0136213 A1 | 5/2017 | Kauphusman et al. |
| 2017/0189643 A1 | 7/2017 | Christian et al. |
| 2017/0203076 A1 | 7/2017 | Groneberg et al. |
| 2017/0215954 A1 | 8/2017 | Datta et al. |
| 2017/0234411 A1 | 8/2017 | Dewaele et al. |
| 2017/0281909 A1 | 10/2017 | Northrop et al. |
| 2018/0015260 A1 | 1/2018 | Sano et al. |
| 2018/0015261 A1 | 1/2018 | Lippert et al. |
| 2018/0015262 A1 | 1/2018 | Lippert et al. |
| 2018/0015263 A1 | 1/2018 | Lippert et al. |
| 2018/0028177 A1 | 2/2018 | Van et al. |
| 2018/0071496 A1 | 3/2018 | Snyder et al. |
| 2018/0177517 A1 | 6/2018 | Lippert et al. |
| 2018/0185619 A1 | 7/2018 | Batman et al. |
| 2018/0193603 A1 | 7/2018 | Falb et al. |
| 2018/0193607 A1 | 7/2018 | Lippert et al. |
| 2018/0207407 A1 | 7/2018 | Tanigaki |
| 2019/0008639 A1 | 1/2019 | Landon et al. |
| 2019/0105463 A1 | 4/2019 | Christian et al. |
| 2019/0255290 A1 | 8/2019 | Snyder et al. |
| 2019/0290883 A1 | 9/2019 | Lippert et al. |
| 2020/0016378 A1 | 1/2020 | Williams et al. |
| 2020/0054860 A1 | 2/2020 | Mcelhaney et al. |
| 2020/0094027 A1 | 3/2020 | Davis |
| 2020/0121308 A1 | 4/2020 | Davis et al. |
| 2020/0222672 A1 | 7/2020 | Davis et al. |
| 2020/0345975 A1 | 11/2020 | Snyder |
| 2021/0162184 A1 | 6/2021 | Lippert et al. |
| 2021/0178128 A1 | 6/2021 | Lippert et al. |
| 2021/0213241 A1 | 7/2021 | Christian et al. |
| 2021/0228845 A1 | 7/2021 | Lippert et al. |
| 2021/0307766 A1 | 10/2021 | Keating et al. |
| 2021/0346656 A1 | 11/2021 | Lippert et al. |
| 2022/0105312 A1 | 4/2022 | Davis |
| 2022/0105318 A1 | 4/2022 | Davis et al. |
| 2022/0118225 A1 | 4/2022 | Snyder et al. |
| 2022/0280147 A1 | 9/2022 | Davis |
| 2022/0296850 A1 | 9/2022 | Lippert |
| 2022/0378459 A1 | 12/2022 | Lippert |
| 2023/0071512 A1 | 3/2023 | Maggio et al. |
| 2023/0082226 A1 | 3/2023 | Lippert et al. |

FOREIGN PATENT DOCUMENTS

| | | |
|---|---|---|
| AU | 07745/59 B2 | 7/2004 |
| AU | 2008229892 A1 | 10/2008 |
| BR | 9709363 A | 1/2000 |
| BR | 9712829 A | 1/2000 |
| CA | 2255781 A1 | 11/1997 |
| CA | 2266685 A1 | 3/1998 |
| CA | 2395149 A1 | 6/2001 |
| CN | 1225282 A | 8/1999 |
| CN | 1230914 A | 10/1999 |
| CN | 1324285 A | 11/2001 |
| CN | 1422673 A | 6/2003 |
| CN | 1518428 A | 8/2004 |
| CN | 1781684 A | 6/2006 |
| CN | 1897892 A | 1/2007 |
| CN | 101001660 A | 7/2007 |
| CN | 101209365 A | 7/2008 |
| CN | 101304778 A | 11/2008 |
| CN | 201239164 Y | 5/2009 |
| CN | 101815553 A | 8/2010 |
| CN | 102049085 A | 5/2011 |
| CN | 102107041 A | 6/2011 |
| CN | 102548603 A | 7/2012 |
| CN | 102629303 A | 8/2012 |
| CN | 102824681 A | 12/2012 |
| CN | 102847225 A | 1/2013 |
| CN | 103301553 A | 9/2013 |
| CN | 103764012 A | 4/2014 |
| CN | 103860265 A | 6/2014 |
| CN | 104271035 A | 1/2015 |
| CN | 104427950 A | 3/2015 |
| CN | 104602616 A | 5/2015 |
| CN | 104461718 A | 5/2015 |
| CN | 104759022 A | 7/2015 |
| CN | 105209102 A | 12/2015 |
| CN | 105545375 A | 5/2016 |
| CN | 105582611 A | 5/2016 |
| CN | 105682725 A | 6/2016 |
| CN | 105682729 A | 6/2016 |
| CN | 105828690 A | 8/2016 |
| CN | 105979880 A | 9/2016 |
| CN | 107206216 A | 9/2017 |
| CN | 109715245 A | 5/2019 |

(56) References Cited

FOREIGN PATENT DOCUMENTS

| | | |
|---|---|---|
| CN | 109789296 A | 5/2019 |
| DE | 60036882 T2 | 7/2008 |
| DE | 69738235 T2 | 7/2008 |
| EP | 0521595 A2 | 1/1993 |
| EP | 0921754 A1 | 6/1999 |
| EP | 0998323 A1 | 5/2000 |
| EP | 0934141 B1 | 11/2005 |
| EP | 1239901 B1 | 10/2007 |
| EP | 1844911 A1 | 10/2007 |
| EP | 1940498 A1 | 7/2008 |
| EP | 2964305 A2 | 1/2016 |
| ES | 2293660 T3 | 3/2008 |
| JP | 59-102509 A | 6/1984 |
| JP | 06-154335 A | 6/1994 |
| JP | 07-008560 A | 1/1995 |
| JP | 08-215313 A | 8/1996 |
| JP | 08-243169 A | 9/1996 |
| JP | 08-308934 A | 11/1996 |
| JP | 11-294497 A | 10/1999 |
| JP | 2000-116787 A | 4/2000 |
| JP | 2000-126301 A | 5/2000 |
| JP | 2000-511094 A | 8/2000 |
| JP | 2000-343313 A | 12/2000 |
| JP | 2001-500808 A | 1/2001 |
| JP | 2002-543896 A | 12/2002 |
| JP | 2003-011117 A | 1/2003 |
| JP | 2004-025340 A | 1/2004 |
| JP | 2004-136121 A | 5/2004 |
| JP | 2004-329552 A | 11/2004 |
| JP | 2004-535233 A | 11/2004 |
| JP | 2005-514115 A | 5/2005 |
| JP | 2005-533594 A | 11/2005 |
| JP | 2005-534407 A | 11/2005 |
| JP | 2007-514458 A | 6/2007 |
| JP | 2007-313638 A | 12/2007 |
| JP | 2008-178656 A | 8/2008 |
| JP | 2008-536639 A | 9/2008 |
| JP | 2010-029736 A | 2/2010 |
| JP | 2010-503484 A | 2/2010 |
| JP | 2010-535583 A | 11/2010 |
| JP | 2010-535588 A | 11/2010 |
| JP | 2011-206175 A | 10/2011 |
| JP | 4805208 B2 | 11/2011 |
| JP | 4845313 B2 | 12/2011 |
| JP | 2012-502743 A | 2/2012 |
| JP | 2013-106854 A | 6/2013 |
| JP | 2013-523282 A | 6/2013 |
| JP | 2013-176560 A | 9/2013 |
| JP | 2014-023727 A | 2/2014 |
| JP | 2015-073861 A | 4/2015 |
| JP | 2015-181723 A | 10/2015 |
| JP | 2015-186427 A | 10/2015 |
| JP | 2016-013269 A | 1/2016 |
| JP | 2017-169253 A | 9/2017 |
| KR | 2000-0015896 A | 3/2000 |
| KR | 10-2000-0036139 A | 6/2000 |
| NO | 99/04847 A1 | 2/1999 |
| TW | 412468 B | 11/2000 |
| WO | 94/06503 A1 | 3/1994 |
| WO | 94/19039 A1 | 9/1994 |
| WO | 95/24237 A2 | 9/1995 |
| WO | 97/43949 A1 | 11/1997 |
| WO | 98/55173 A1 | 12/1998 |
| WO | 98/58697 A1 | 12/1998 |
| WO | 99/53824 A2 | 10/1999 |
| WO | 2004/011076 A2 | 2/2004 |
| WO | 2006/025931 A1 | 3/2006 |
| WO | 2006/058234 A2 | 6/2006 |
| WO | 2006/113863 A2 | 10/2006 |
| WO | 2007/050718 A1 | 5/2007 |
| WO | 2008/034010 A2 | 3/2008 |
| WO | 2009/020691 A2 | 2/2009 |
| WO | 2009/020836 A1 | 2/2009 |
| WO | 2009/020961 A1 | 2/2009 |
| WO | 2009/020962 A1 | 2/2009 |
| WO | 2009/143160 A1 | 11/2009 |
| WO | 2010/077692 A2 | 7/2010 |
| WO | 2010/115163 A1 | 10/2010 |
| WO | 2011/123689 A1 | 10/2011 |
| WO | 2014/005095 A1 | 1/2014 |
| WO | 2014/066104 A1 | 5/2014 |
| WO | 2014/138580 A2 | 9/2014 |
| WO | 2016/047499 A1 | 3/2016 |
| WO | 2016/117238 A1 | 7/2016 |
| WO | 2016/136609 A1 | 9/2016 |
| WO | 2016/152194 A1 | 9/2016 |
| WO | 2016/158671 A1 | 10/2016 |
| WO | 2017/151292 A1 | 9/2017 |
| WO | 2018/017349 A1 | 1/2018 |
| WO | 2018/017351 A1 | 1/2018 |
| WO | 2018/218216 | 11/2018 |
| WO | 2020/217171 A1 | 10/2020 |
| WO | 2022/159139 A1 | 7/2022 |

OTHER PUBLICATIONS

Final Office Action received for U.S. Appl. No. 16/742,211, dated Mar. 14, 2023, 22 pages.
International Search Report and Written Opinion received for PCT Patent Application No. PCT/US22/42514, dated Dec. 28, 2022, 11 pages.
International Search Report and Written Opinion received for PCT Patent Application No. PCT/US22/42517, dated Feb. 7, 2023, 11 pages.
International Search Report and Written Opinion received for PCT Patent Application No. PCT/US2009/067217, dated Dec. 16, 2010, 10 pages.
International Search Report and Written Opinion received for PCT Patent Application No. PCT/US2018/034756, dated Aug. 14, 2018, 12 pages.
International Search Report and Written Opinion received for PCT Patent Application No. PCT/US2021/053647, dated Dec. 28, 2021, 9 pages.
International Search Report and Written Opinion received for PCT Patent Application No. PCT/US2021/053652, dated Dec. 28, 2021, 9 pages.
Final Office Action received for U.S. Appl. No. 12/753,831, dated May 31, 2012.
Final Office Action received for U.S. Appl. No. 12/753,836 dated Feb. 17, 2016.
Final Office Action received for U.S. Appl. No. 16/212,425, dated Aug. 3, 2020, 14 pages.
Final Office Action received for U.S. Appl. No. 12/753,831, dated Aug. 29, 2014.
Final Office Action received for U.S. Appl. No. 12/753,836, dated Jan. 9, 2015.
Final Office Action received for U.S. Appl. No. 12/753,836, dated Jul. 14, 2017.
Final Office Action received for U.S. Appl. No. 12/753,836, dated May 1, 2012.
Final Office Action received for U.S. Appl. No. 12/753,839, dated May 31, 2012.
Final Office Action received for U.S. Appl. No. 12/753,842, dated Jan. 9, 2013.
Final Office Action received for U.S. Appl. No. 12/753,842, dated Sep. 4, 2014.
Final Office Action received for U.S. Appl. No. 12/753,849, dated Jun. 6, 2012.
Final Office Action received for U.S. Appl. No. 12/753,849, dated Oct. 9, 2013.
Final Office Action received for U.S. Appl. No. 12/753,855, dated Apr. 18, 2012.
Final Office Action received for U.S. Appl. No. 12/753,855, dated Jan. 13, 2015.
Final Office Action received for U.S. Appl. No. 12/753,858, dated Jan. 17, 2014.
Final Office Action received for U.S. Appl. No. 12/753,858, dated Jul. 18, 2012.

(56) References Cited

OTHER PUBLICATIONS

Final Office Action received for U.S. Appl. No. 12/753,858, dated May 28, 2015.
Final Office Action received for U.S. Appl. No. 12/753,858, dated Nov. 14, 2018.
Final Office Action received for U.S. Appl. No. 12/753,858, dated Oct. 19, 2011.
Final Office Action received for U.S. Appl. No. 12/753,858, dated Oct. 20, 2017.
Final Office Action received for U.S. Appl. No. 15/606,607, dated Nov. 19, 2019.
Final Office Action received for U.S. Appl. No. 15/611,344, dated Nov. 12, 2019.
Final Office Action received for U.S. Appl. No. 15/848,878, dated Aug. 27, 2020, 13 pages.
Final Office Action received for U.S. Appl. No. 16/281,046, dated May 11, 2021, 18 pages.
Final Office Action received for U.S. Appl. No. 14/199,675, dated May 18, 2017.
Final Office Action received for U.S. Appl. No. 15/611,328, dated Sep. 24, 2019.
Final Office Action received for U.S. Appl. No. 15/698,553, dated Nov. 27, 2019.
Final Rejection received for U.S. Appl. No. 15/606,607, dated Dec. 15, 2020, 24 pages.
International Search Report and Written Opinion for application No. PCT/US17/41305 dated Oct. 2, 2017.
International Search Report and Written Opinion for Application PCT/US2017/050602 dated Nov. 7, 2017.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/041299 dated Oct. 2, 2017.
International Search Report and Written Opinion for PCT/US2017/041301 dated Oct. 2, 2017.
International Search Report and Written Opinion for PCT/US2017/068056 dated Feb. 26, 2018.
International Search Report and Written Opinion for PCT/US2018/034756 dated Aug. 14, 2018.
International Search Report and Written Opinion for PCT/US2019/019046, dated May 17, 2019.
International Search Report and Written Opinion for PCT/US2019/021031 dated Jun. 18, 2019.
International Search Report and Written Opinion issued in PCT/US2018/034723 dated Sep. 5, 2018.
International Search Report and Written Opinion received for PCT Patent Application No. PCT/US2020/030589, dated Jul. 17, 2020, 7 pages.
International Search Report and Written Opinion received for PCT Patent Application No. PCT/US21/14656, dated Apr. 28, 2021, 8 pages.
International Search Report and Written Opinion, PCT App. No. PCT/US2020/013754, dated Jun. 9, 2020, 11 pages.
InternationalSearch Report and Written Opinion for application PCT/US2017/050802 dated Nov. 7, 2017.
Non-Final Office Action received for U.S. Appl. No. 15/606,607, dated Jun. 10, 2020, 26 pages.
Non-Final Office Action received for U.S. Appl. No. 15/611,328, dated Jun. 29, 2020, 13 pages.
Non-Final Office Action received for U.S. Appl. No. 15/848,878, dated Jun. 3, 2021, 13 pages.
Non-Final Office Action received for U.S. Appl. No. 15/917,255, dated Aug. 17, 2020, 12 pages.
Non-Final Office Action received for U.S. Appl. No. 16/281,046, dated Oct. 29, 2020, 18 pages.
Final Office Action received for U.S. Appl. No. 16/616,220, dated Oct. 12, 2022, 17 pages.
Final Office Action received for U.S. Appl. No. 16/855,366, dated Dec. 8, 2022, 18 pages.
Non-Final Office Action received for U.S. Appl. No. 16/742,211, dated Aug. 15, 2022, 20 pages.
Non-Final Office Action received for U.S. Appl. No. 17/177,782, dated Jan. 23, 2023, 14 pages.
Non-Final Office Action received for U.S. Appl. No. 17/177,782, dated Nov. 4, 2022, 7 pages.
Final Office Action received for U.S. Appl. No. 17/216,127, dated Jun. 13, 2022, 8 pages.
International Search Report and Written Opinion received for PCT Patent Application No. PCT/US21/042753, dated Nov. 5, 2021, 14 pages.
Non-Final Office Action received for U.S. Appl. No. 16/616,139, dated Oct. 26, 2021, 11 pages.
Non-Final Office Action received for U.S. Appl. No. 16/616,220, dated Jun. 3, 2022, 20 pages.
Non-Final Office Action received for U.S. Appl. No. 16/855,366, dated Jul. 11, 2022, 13 pages.
Non-Final Office Action received for U.S. Appl. No. 16/855,366, dated Jun. 23, 2021, 15 pages.
Notice of Allowance received for U.S. Appl. No. 16/212,425, dated Dec. 23, 2020, 12 pages.
Notice of Allowance received for U.S. Appl. No. 16/212,425, dated Jan. 25, 2021, 2 pages.
Office Action received for U.S. Appl. No. 12/633,727, dated Oct. 16, 2012.
Office Action received for U.S. Appl. No. 12/753,831, dated Feb. 1, 2012.
Office Action received for U.S. Appl. No. 12/753,831, dated Mar. 21, 2014.
Office Action received for U.S. Appl. No. 12/753,836, dated Dec. 9, 2011.
Office Action received for U.S. Appl. No. 12/753,836, dated Dec. 23, 2016.
Office Action received for U.S. Appl. No. 12/753,836, dated Jul. 31, 2014.
Office Action received for U.S. Appl. No. 12/753,836, dated Jun. 26, 2015.
Office Action received for U.S. Appl. No. 12/753,839, dated Feb. 7, 2012.
Office Action received for U.S. Appl. No. 12/753,839, dated May 5, 2014.
Office Action received for U.S. Appl. No. 12/753,842, dated Aug. 1, 2012.
Office Action received for U.S. Appl. No. 12/753,842, dated Jan. 29, 2014.
Office Action received for U.S. Appl. No. 12/753,849, dated Jan. 3, 2013.
Office Action received for U.S. Appl. No. 12/753,849, dated May 10, 2011.
Office Action received for U.S. Appl. No. 12/753,849, dated May 27, 2014.
Office Action received for U.S. Appl. No. 12/753,849, dated Oct. 18, 2011.
Office Action received for U.S. Appl. No. 12/753,855, dated Feb. 28, 2014.
Office Action received for U.S. Appl. No. 12/753,855, dated May 21, 2015.
Office Action received for U.S. Appl. No. 12/753,855, dated Sep. 15, 2011.
Office Action received for U.S. Appl. No. 12/753,858, dated Dec. 30, 2015.
Office Action received for U.S. Appl. No. 12/753,858, dated Feb. 3, 2012.
Office Action received for U.S. Appl. No. 12/753,858, dated Mar. 13, 2018.
Office Action received for U.S. Appl. No. 12/753,858, dated Mar. 27, 2017.
Office Action received for U.S. Appl. No. 12/753,858, dated Mar. 29, 2013.

(56) References Cited

OTHER PUBLICATIONS

Office Action received for U.S. Appl. No. 12/753,858, dated May 10, 2011.
Office Action received for U.S. Appl. No. 12/753,858, dated Oct. 24, 2016.
Office Action received for U.S. Appl. No. 12/753,858, dated Sep. 4, 2014.
Office Action received for U.S. Appl. No. 13/901,375, dated Dec. 10, 2015.
Office Action received for U.S. Appl. No. 15/465,399, dated Apr. 23, 2018.
Office Action received for U.S. Appl. No. 15/606,607, dated May 14, 2019.
Office Action received for U.S. Appl. No. 15/611,344, dated Mar. 26, 2019.
Office Action received for U.S. Appl. No. 15/611,344, dated May 21, 2020.
Office Action received for U.S. Appl. No. 15/848,878, dated Feb. 5, 2020.
Office Action received for U.S. Appl. No. 15/848,878, dated Oct. 29, 2019.
Office Action received for U.S. Appl. No. 16/212,425, dated Mar. 16, 2020.
Office Action received for U.S. Appl. No. 12/753,855 dated May 5, 2016.
Office Action received for U.S. Appl. No. 13/901,375, dated Aug. 1, 2016.
Office Action received for U.S. Appl. No. 14/199,675, dated Nov. 3, 2016.
Office Action received for U.S. Appl. No. 15/611,328, dated Mar. 27, 2019.
Office Action received for European Patent Application No. 19710207.2, dated Dec. 4, 2023, 4 pages.
Supplementary European Search Report received for EP Patent Application No. 21744674.9, dated Feb. 7, 2024, 9 pages.

* cited by examiner

GUIDEWIRE DEVICES HAVING SHAPEABLE TIPS AND BYPASS CUTS

CROSS-REFERENCE TO RELATED APPLICATIONS

This application is a divisional of U.S. patent application Ser. No. 15/917,255, filed Mar. 9, 2018 and titled "GUIDEWIRE DEVICES HAVING SHAPEABLE TIPS AND BYPASS CUTS", which is a continuation-in-part of U.S. patent application Ser. No. 15/606,607, filed May 26, 2017 and titled "GUIDEWIRE DEVICES HAVING SHAPEABLE TIPS," which claims priority to and the benefit of U.S. Provisional Patent Application Ser. No. 62/363,760, filed Jul. 18, 2016 and titled "GUIDEWIRE DEVICES HAVING SHAPEABLE TIPS," each of which are incorporated by reference in their entirety.

BACKGROUND

Guidewire devices are often used to lead or guide catheters or other interventional devices to a targeted anatomical location within a patient's body. Typically, guidewires are passed into and through a patient's vasculature in order to reach the target location, which may be at or near the patient's heart or neurovascular tissue, for example. Radiographic imaging is typically utilized to assist in navigating a guidewire to the targeted location. In many instances, a guidewire is left in place within the body during the interventional procedure where it can be used to guide multiple catheters or other interventional devices to the targeted anatomical location.

Some guidewire devices are constructed with a curved or bent tip to enable an operator to better navigate a patient's vasculature. With such guidewires, an operator can apply a torque to the proximal end of the guidewire or attached proximal handle in order to orient and point the tip in a desired direction. The operator may then direct the guidewire further within the patient's vasculature in the desired direction.

Tuning the flexibility of a guidewire device, particularly the distal sections of the guidewire device, is also a concern. In many circumstances, relatively high levels of flexibility are desirable in order to provide sufficient bendability of the guidewire to enable the guidewire to be angled through the tortuous bends and curves of a vasculature passageway to arrive at the targeted area. For example, directing a guidewire to portions of the neurovasculature requires passage of the guidewire through curved passages such as the carotid siphon and other tortuous paths.

Another concern related to guidewire devices is the ability of a given guidewire device to transmit torque from the proximal portion to the distal portion (i.e., the "torquability" of the guidewire device). As more of a guidewire is passed into and through a tortuous vasculature passageway, the amount of frictional surface contact between the guidewire and the vasculature increases, hindering easy movement of the guidewire through the vasculature passage. A guidewire with good torquability enables torqueing forces at the proximal end to be transmitted through the guidewire to the distal end so that the guidewire can rotate and overcome the frictional forces.

Some guidewire devices include a distally placed micromachined hypotube positioned over the distal end of the guidewire core in order to direct applied torsional forces further distally toward the end of the device. Because torsional forces are primarily transmitted through the outer sections of a cross-section of a member, the tube is configured to provide a path for increased transmission of torque as compared to the amount of torque transmitted by a guidewire core not sheathed by a tube. Typically, such tubes are formed from a superelastic material such as nitinol so as to provide desired torque transmission characteristics in addition to providing good levels of flexibility.

While such guidewire devices have provided many benefits, several limitations remain. For example, many of the design characteristics of a guidewire having a torque-transmitting tube, although functioning to provide increased torque transmission, work against and limit the shapeability of the guidewire tip.

BRIEF SUMMARY

The present disclosure relates to guidewire devices having shapeable tips and effective torquability. In one embodiment, a guidewire device includes a core having a proximal section and a tapered distal section. A tube structure is coupled to the core such that the tapered distal section extends into the tube structure. The tube structure includes a plurality of bypass cuts formed tangentially within the tube structure to increase the flexibility of the tube structure and to reduce the tendency of resilient forces from the tube structure to disrupt a shaped distal tip of the guidewire device. The bypass cuts are part of a cut pattern which forms a plurality of axially extending beams coupling a plurality of circumferentially and transversely extending rings. The bypass cuts form a one-beam cut pattern which forms a single beam between each adjacent ring within the one-beam cut pattern.

Some embodiments further include a coil disposed within the tube structure so as to be positioned between an outer surface of the distal section of the core and an inner surface of the tube structure. The coil may be formed from a radiopaque material, such as platinum. In some embodiments, the core is formed from stainless steel, and the tube structure is formed from a superelastic material such as nitinol.

In some embodiments, at least a portion of the cut pattern includes a one-sided one-beam cut pattern wherein a plurality of successive beams are disposed on a single side of the tube structure with respect to a longitudinal axis of the guidewire device. In some embodiments, the cut pattern includes a two-beam cut pattern disposed proximal of the one-beam cut pattern. The two-beam cut pattern may include a depth-symmetric two-beam cut pattern and a depth-offset two-beam cut pattern, with the depth-symmetric two-beam cut pattern disposed proximal of the depth-offset two-beam cut pattern such that the depth-offset two-beam cut pattern functions as a transition between the one-beam cut pattern and the depth-symmetric two-beam cut pattern.

In some embodiments, the one-beam cut pattern is arranged with cuts of increasing depth toward a distal end of the tube structure and/or is arranged such that spacing between successive cuts decreases toward a distal end of the tube structure.

In some embodiments, the distal section of the core is formed from a shapeable material and is configured to have a stiffness such that when the distal tip is bent into a shaped configuration, the distal section of the core is able to withstand deformation caused by an elastic recovery force of the tube structure.

In one embodiment, the tube structure includes a first section and a second section, the second section being distal to the first section. At the second section of the tube, the cutting pattern forms a single beam between each pair of adjacent rings. The beams of the second section are arranged to form a preferred bending plane (e.g., by each successive beam being rotated approximately 180 degrees relative to the previous beam). The tube is least resistant to bending within the preferred bending plane. In this embodiment, the distal section of the core passes through the second section of the tube and tapers to a flat ribbon that coincides with at least a portion. The flat ribbon of the core has a major plane that lies perpendicular to the preferred bending plane of the second section of the tube.

In another embodiment, the tube structure includes a first and second section separated by a transition point, with the second section distal to the first section. The first section includes a two-beam cutting pattern and the second section includes a one-beam cutting pattern. The two-beam cutting pattern immediately proximal of the transition point and the one-beam cutting pattern immediately distal of the transition point are configured such that the stiffness profile of the tube remains approximately the same across the transition between the first and second sections. Also, in this embodiment, the thickness of the most proximal ring in the second section is greater than the thickness of the most distal ring of the first section.

In another embodiment, the tube includes a first section, a second section distal of the first section, and a third section distal of the second section. The first section includes a two-beam section, the second section includes a one-beam cutting pattern, and the third section includes a two-beam cutting pattern. As measured from the distal end of the tube, the third section extends from about 0.25 mm and 2.5 mm proximally.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

A more particular description of the invention briefly described above will be rendered by reference to specific embodiments which are illustrated in the appended drawings. Understanding that these drawings depict only typical embodiments of the invention and are not limiting of its scope, the invention will be described and explained with additional specificity and detail through the use of the accompanying drawings in which.

DETAILED DESCRIPTION

The present disclosure relates to guidewire devices providing effective anatomical navigation capabilities. The ability to steer and direct a guidewire to a targeted anatomical location depends on balancing and optimizing tradeoffs between torquability and the ability to maintain a shaped tip. A guidewire device may include a shapeable tip to allow an operator to point the tip in a desired direction within the vasculature by rotating the distal tip. However, if the torquability of such a guidewire device is insufficient, the operator will be unable to transmit torsional forces all the way to the shaped distal tip to control the orientation of the shaped distal tip. This hindrance will become increasingly problematic as the guidewire device is advanced farther into the vasculature and experiences increasing frictional resistance. In addition, if a guidewire device is unable to properly form and maintain a shaped tip, it will have limited ability to adjust tip orientation, making intravascular navigation more difficult.

Embodiments described herein provide one or more features that balance and/or optimize the relationship between guidewire torquability and the ability to form and maintain a shaped tip. Such guidewires are responsive to operator manipulation during guidewire deployment, and provide effective navigation capabilities by enabling a shaped distal tip to receive transmitted torsional forces.

In some embodiments, the shapeable tip allows an operator to custom shape the tip, such as by manually shaping the tip just prior to deploying the guidewire device within the patient's vasculature. The operator is thus enabled to customize the shaping of the distal tip according to preferences and/or conditions particular to a given application. The guidewire device is also configured to effectively transmit torque while maintaining the shaped tip. At least some embodiments described herein include tips that are able to maintain a bent or curved shape throughout a procedure, or throughout multiple procedures, or even indefinitely until subjected to a counteracting reshaping force.

Figure 1:
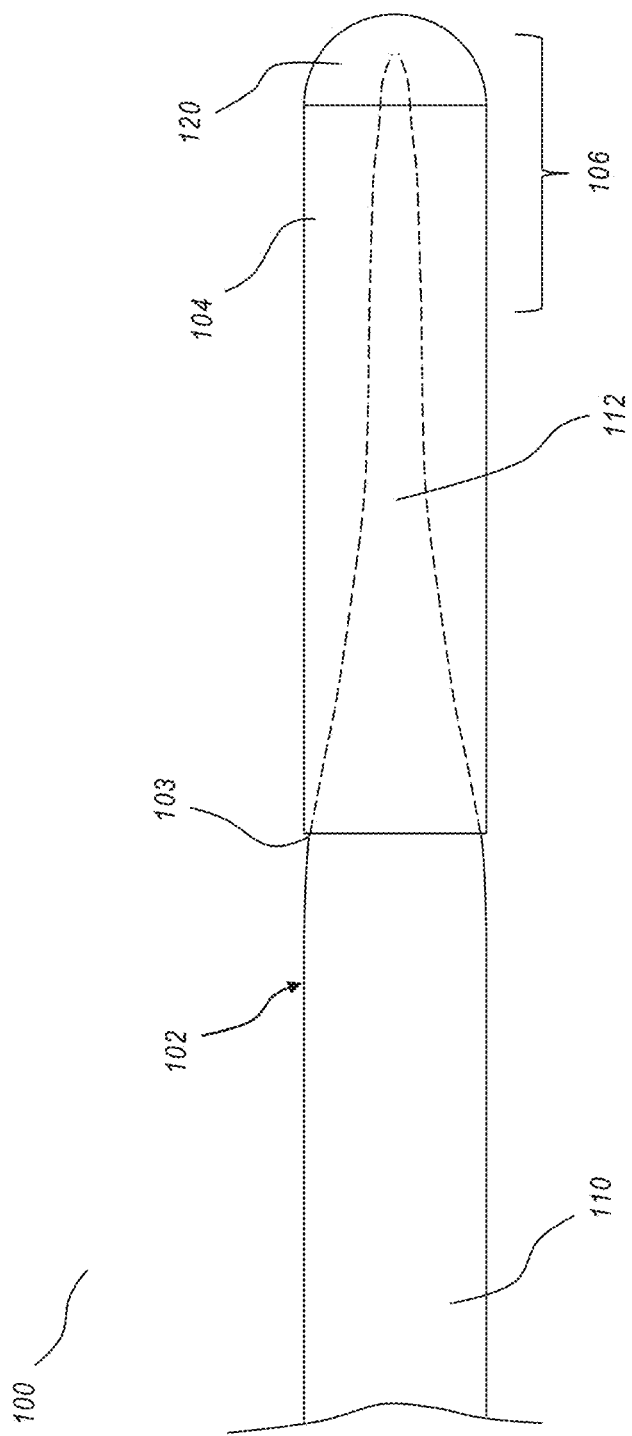
FIG. 1 illustrates an exemplary embodiment of a guidewire device providing effective torquability and having a shapeable tip.

FIG. 1 illustrates an exemplary guidewire device 100 having a core 102. A tube 104 is coupled to the core 102 and extends distally from a point of attachment 103 to the core 102. As shown, a distal section of the core 102 extends into the tube 104 and is surrounded by the tube 104. In some embodiments, the core 102 includes one or more tapering sections so that the core 102 is able to fit within and extend into the tube 104. For example, the distal section of the core 102 may be ground so as to progressively taper to a smaller diameter at the distal end. In this example, the core 102 and the tube 104 have substantially similar outer diameters at the attachment point 103 where they adjoin and attach to one another. In some embodiments, the core 102 and the tube 104 have different outer diameters at the attachment point 103 where they adjoin and attach to one another, with the difference in diameter being compensated for by a weld, solder, adhesive, interference fit, or other means of structural attachment.

Figure 3:
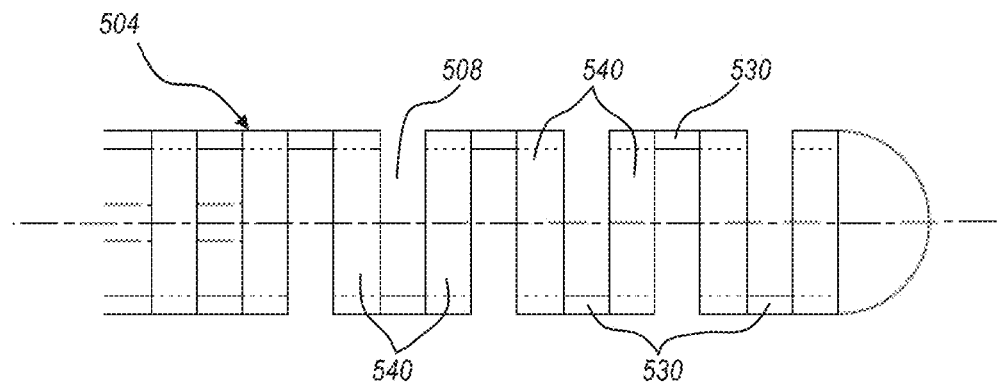
FIG. 3 illustrates an exemplary embodiment of a tube structure which may be utilized with the guidewire device of FIGS. 1 and 2, the tube having a bypass cut pattern (i.e., one-beam cut pattern) configured to provide effective flexibility and shapeability of the distal tip.
Figure 4:
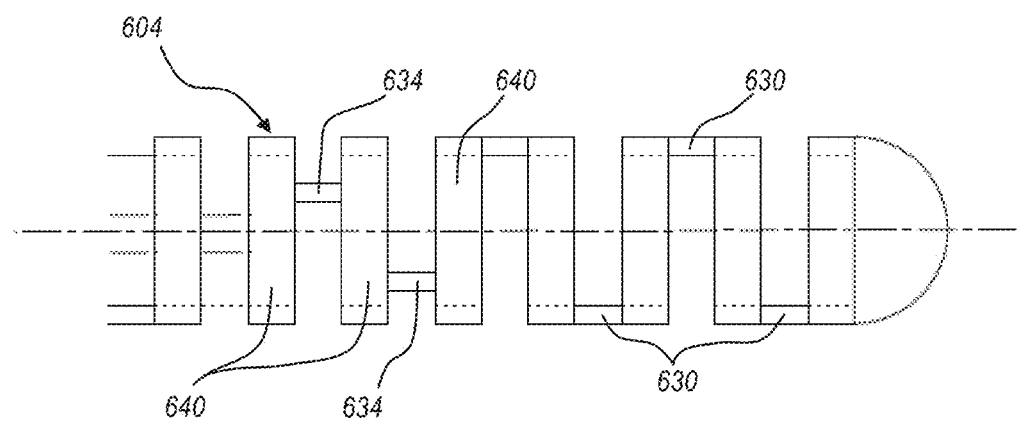
FIG. 4 illustrates an alternative embodiment of a tube structure including a section having an alternative one-beam cut pattern.
Figure 5:
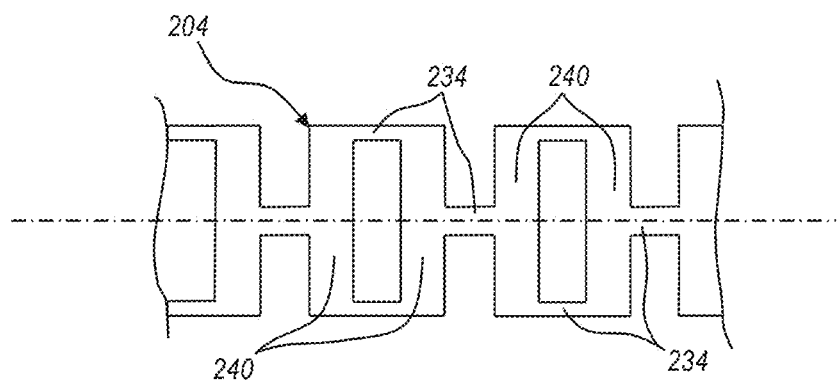
FIG. 5 illustrates an embodiment of a tube structure including a two-beam cut pattern with symmetrically spaced opposing beams.

The tube 104 is coupled to the core 102 (e.g., using adhesive, soldering, and/or welding) in a manner that allows torsional forces to be transmitted from the core 102 to the tube 104 and thereby to be further transmitted distally by the tube 104. A medical grade adhesive 120 may be used to couple the tube 104 to the core wire 102 at the distal end of the device and to form an atraumatic covering. As explained in more detail below, the tube 104 is micro-fabricated to include a plurality of cuts. The cuts are arranged to form a cut pattern which beneficially provides for effective shapeability near the distal tip of the guidewire device 100 while also maintaining good torquability. For clarity, the cut pattern is not shown in FIGS. 1 and 2. Examples of cut patterns which may be utilized in the tube 104 are shown in FIGS. 3 through 5.

The proximal section 110 of the guidewire device 100 extends proximally to a length necessary to provide sufficient guidewire length for delivery to a targeted anatomical area. The proximal section 110 typically has a length ranging from about 50 to 350 cm. The proximal section 110 may have a diameter of about 0.014 inches, or a diameter within a range of about 0.008 to 0.125 inches. The distal section 112 of the core 102 may taper to a diameter of about 0.002 inches, or a diameter within a range of about 0.001 to 0.050 inches. In some embodiments, the tube 104 has a length within a range of about 3 to 100 cm.

In some embodiments, the distal section 112 of the core 102 tapers to a round cross-section. In other embodiments, the distal section 112 of the core 102 has a flat or rectangular cross-section. The distal section 112 may also have another cross-sectional shape, such as another polygon shape, an ovoid shape, an erratic shape, or combination of different cross-sectional shapes at different areas along its length.

Typically, a user will shape the distal end of the guidewire device 100 by manually bending, twisting, or otherwise manipulating the distal 1 cm to 3 cm (approximately) of the guidewire device 100 to a desired shape. This length is shown schematically as the distal "tip" 106 in FIG. 1. In some embodiments, the tip 106 includes one or more shapeable components (within the tube 104) formed from stainless steel, platinum, and/or other shapeable materials. In preferred embodiments, the tip 106 includes one or more components formed from a material that exhibits work hardening properties, such that the tip, when shaped (i.e., plastically deformed), provides a higher elastic modulus at the shaped sections than prior to being shaped.

Figure 2:
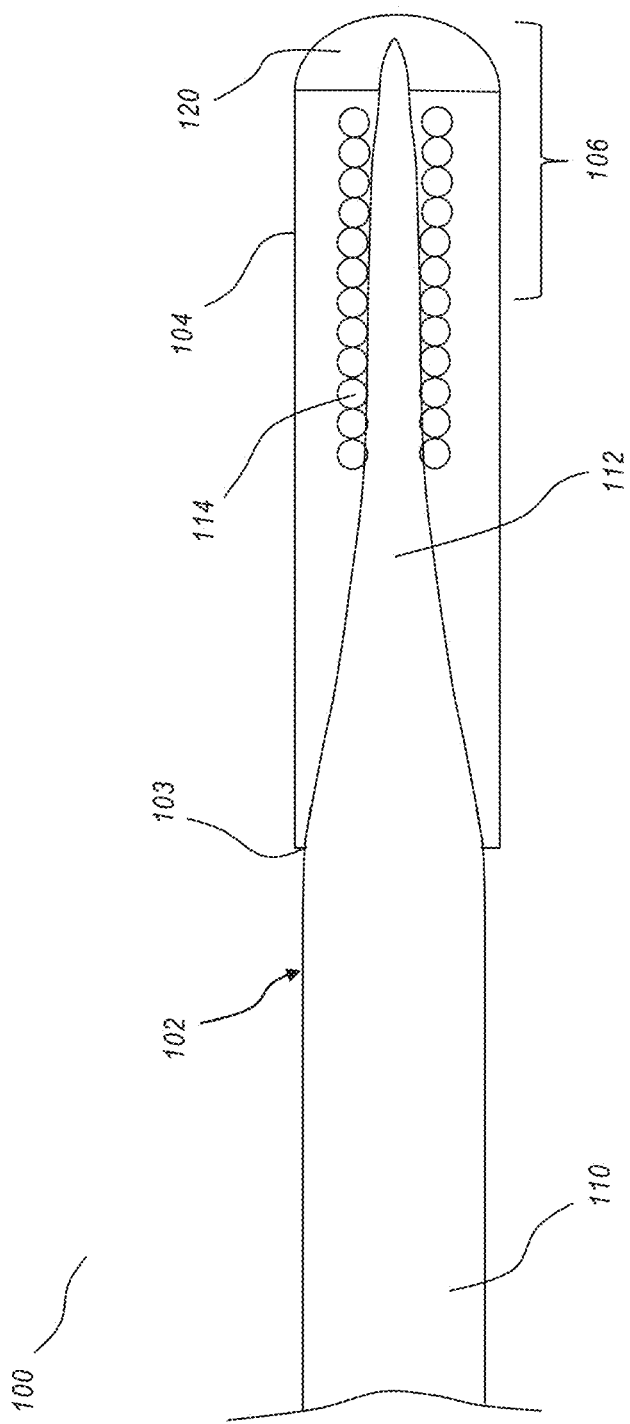
FIG. 2 is a cross-sectional view of the guidewire device of FIG. 1.

FIG. 2 illustrates a cross-sectional view of the guidewire device 100 of FIG. 1. As shown, the core 102 includes a proximal section 110 and a distal section 112, with the distal section having a smaller diameter than the proximal section 110. A coil 114 is positioned upon at least a portion of the distal section 112 of the core 102. The coil 114 is preferably formed from one or more radiopaque materials, such as platinum group, gold, silver, palladium, iridium, osmium, tantalum, tungsten, bismuth, dysprosium, gadolinium, and the like. Additionally, or alternatively, the coil 114 may be at least partially formed from a stainless steel or other material capable of effectively holding shaped after being bent or otherwise manipulated by a user. In the illustrated embodiment, the coil 114 is disposed at or near the distal end of the device and extends a distance proximally toward the attachment point 103. In some embodiments, the coil 114 has a length that substantially coincides with the length of the tube 104. In other embodiments, the coil 114 is shorter. For example, the coil 114 may extend from the distal end by 1, 2, 4, 6, 8, 10, 12, 15, 20, 25, 30, or 35 cm, or may extend from the proximal end a distance within a range defined by any two of the foregoing values.

In some embodiments, the coil 114 is formed as one integral piece. In other embodiments, the coil 114 includes a plurality of separate sections positioned adjacent to one another and/or interlocked through intertwining coils. Such separate segments may additionally or alternatively be soldered, adhered, or otherwise fastened to one another to form the complete coil 114. Some embodiments may include two or more coils, where at least one of the coils is configured to provide radiopacity and at least one of the coils is configured in size and shape to improve centering of the distal section 112 of the core 102 inside the tube 104.

Although the illustrated embodiment shows a space between the coil 114 and the tube 104, it will be understood that this is done schematically for ease of visualization. In some embodiments, the coil 114 is sized to fill and pack a greater proportion of the space between the distal section 112 and the tube 104. For example, the coil 114 may be sized so as to abut both the distal section 112 of the core 102 and the inner surface of the tube 104. Other embodiments include a space between the core 102 and the tube 104 for at least a portion of the section of the guidewire device 100 where the tube 104 and the core 102 are co-extensive.

The coil 114 may beneficially function to pack the space between the core 102 and the tube 104 so as to align the curvature of the distal section 112 of the core 102 with the curvature of the tube 104. For example, when a curvature is formed in the tube 104, the closely packed segments of the coil 114 functions as a packing between the tube 104 and the distal section 112 to impart the same curvature to the distal section 112. In contrast, a guidewire device omitting a coil, when curved at the tube, would not follow the same curve as the tube but would extend until abutting against the inner surface of the tube before being forced to curve.

Embodiments described herein beneficially allow the distal tip 106 to be shaped to a desired position and to remain in the shaped position for a sufficiently extended period of time. In contrast to a conventional guidewire device, the illustrated embodiments are able to form and maintain a shaped configuration. With conventional guidewire devices, problems related to shapeability often occur as a result of a mismatch in properties between the tube structure and the internal components (the core and coil). Tube structures are typically formed from nitinol or other superelastic materials. Such tubes will be, upon being bent or shaped, biased toward their original (straight) position, and will thereby impart recovery forces against any shapeable internal components, resulting in deformation and a loss of the customized shape of the tip.

Often, for example, a conventional guidewire will have a shaped tip prior to deployment, but the shaped tip will be lost or degraded during use of the guidewire as the superelastic tube flexes toward its original shape in opposition to the desired tip shape. The recovery forces imparted by the tube thus act against the internal components to reduce or degrade the desired shape set by the user. In contrast, the embodiments described herein includes features that enable the tip 106 to be shaped without being subjected to overriding recovery forces from the tube. As described below, the tube 104 may include a cut pattern which maintains effective torquability while also providing sufficient flexibility at the distal tip 106 so as to avoid disrupting the custom shape of the tip 106.

FIGS. 3 through 7 illustrate exemplary embodiments of tube cut patterns that may be utilized in one or more of the guidewire device embodiments described herein. For example, the tube 104 of the embodiment shown in FIGS. 1 and 2 may be cut according to one or more of the configurations shown in FIGS. 3 through 7.

FIG. 3 illustrates a tube 504 having a series of cuts 508 which form beams 530 (extending axially) and rings 540 (extending transversely and circumferentially). In the illustrated embodiments, the cuts 508 are arranged on the tube as a series of "bypass cuts." As used herein, a bypass cut is a cut that does not have an opposing cut directly opposite of it with respect to the longitudinal axis of the tube, thereby leaving a single beam 530 of longitudinally extending material between rings 540 of transversely and circumferentially extending material. A "bypass" cut pattern may also be referred to herein as a "one-beam" cut pattern. The transverse cross-sectional geometries of the beams can be a variety of shapes including semi-circular such as those made from a cutting saw with a circular blade, flat sided such as those made from a laser machining operation, or any type of cross sectional shape. In the illustrated embodiment, the cuts are arranged as alternating cuts that are offset by about 180 degrees from one cut to the next along the length of the tube 504, but rotational offsets can also be made at angles that are different than 180 degrees to 0 degrees as described below.

Tubes formed using one or more sections of bypass (i.e., one-beam) cuts as shown can provide a number of benefits, particularly with respect to an associated shapeable tip of a guidewire device. For example, the flexibility of a tube having bypass cuts is relatively greater than the flexibility of a tube having no cuts or having cuts which leave multiple beams between successive rings (e.g., assuming beam width, ring size, and cut spacing is otherwise equal). Beneficially, the increased flexibility provided by the bypass cut arrangement minimizes or prevents the tube from deforming the shape of the internal structures of the guidewire. For example, a core (e.g. stainless steel) disposed within a tube may be bent or curved (i.e., plastically deformed) so as to provide the tip of the guidewire with a desired shape.

As explained above, in many instances, forces associated with elastic recovery of the tube will be imparted against the shaped core and will tend to straighten out the shaped core, at least with respect to the portions of the shaped core that are disposed within the tube. Appropriately tuning the flexibility of the tube therefore reduces the recovery force imparted against the shaped core and allows the shaped core to better maintain its shape.

In some embodiments, the depth of successive bypass cuts or sets of bypass cuts is progressively increased for each successive cut or sets of cuts moving toward the distal end. A cut depth profile can therefore be utilized to configure a tube with the desired flexibility and torquability characteristics for a given application. For example, one tube configuration can include a proximal section with relatively lower flexibility and relatively higher torquability that rapidly progresses to a distal section with relatively higher flexibility and relatively lower torquability as bypass cuts rapidly get progressively deeper toward the distal end. In some embodiments, the section having relatively deeper cuts is formed only at the distal-most section of the tube where shapeability is expected or desired (e.g., the distal 1 to 3 cm of the tube), so as to preserve higher torquability for the remainder of the tube.

Bypass cuts 508 may be varied according to depth, width, and/or spacing. For example, cuts 508 may get progressively deeper and/or more closely spaced the closer they get to the distal tip of the device. Cuts that are deeper and/or more closely spaced provide relatively greater flexibility. Thus, a gradient may be formed which provides for increasing guidewire flexibility at progressively more distal regions of the guidewire. As described in more detail below, bypass cuts 508 may also be arranged with alternating angular positions according to an angular offset applied at each adjacent cut or applied at adjacent sets of cuts. The illustrated embodiment shows an angular offset of 180 degrees from one cut to the next. Some embodiments may include an angular offset of about 5, 15, 30, 45, 60, 75, 80, or 85 degrees from one cut to the next or from one set of cuts to the next set of cuts.

FIG. 4 illustrates another embodiment of a tube 604 having bypass cuts and a set of opposing, depth-offset two-beam cuts disposed proximal to the bypass cuts. In the illustrated embodiment, a set of bypass cuts results in the beams 630. Proximal to the beams 630 is a set of cuts arranged as opposing cuts which result in beams 634. Although not visible in this view, an additional beam is formed opposite each beam 634 (hidden behind beams 634 in this view). Each ring 640 within the depth-offset two-beam cut pattern therefore has a set of two beams connecting it to its proximally adjacent ring, and a set of two beams connecting it to its distally adjacent ring.

As shown, the opposing two-beam cuts are offset in depth so that, for each opposing cut pair (one cut on each side of the tube axis), one of the cuts has a depth that is greater than the opposite cut. Such depth-offset two-beam cuts may be advantageously used to transition from a length of bypass cuts (such as shown in FIG. 3) to a length of non-offset opposing two-beam cuts (such as shown in FIG. 5).

FIG. 5 illustrates a section of tube 204 having a two-beam cut pattern, with each cut of each opposing cut pair having approximately the same cut depth so that the resulting beams are substantially equally circumferentially spaced. As shown, the cuts result in a pair of beams 234 formed between each of the rings 240. The cuts are shown here as being angularly offset by about 90 degrees from one pair of opposing cuts to the next, though other angular offsets may be utilized.

A section of tube having a two-beam cut pattern with substantially circumferentially equally spaced beams will typically have relatively higher ability to transmit torque and relatively lower flexibility, while a section of tube having bypass cuts will typically have relatively lower ability to transmit torque and relatively higher flexibility. A section of tube having a depth-offset two-beam cut configuration will typically have a torque transmissibility and flexibility between that of a section of depth-symmetric opposing two-beam cuts and a section of bypass cuts. The greater the difference between the depths of opposing cuts, the closer together circumferentially the resulting beams will be, and therefore the more similar the offset two-beam cut will be to a one-beam/bypass cut. Likewise, the more similar the depths of the opposing cuts are, the more similar the offset two-beam cut will be to a symmetric two-beam cut.

Embodiments of tubes including an offset two-beam section advantageously provide a transition zone that may be positioned and configured to provide desired transition properties between a distal bypass cut zone and a proximal symmetric two-beam section. For example, the transition zone may be relatively gradual or abrupt, depending on the length of the transition zone and/or depending on the rapidity of change to the offset in successive cuts. Tubes may therefore be configured to provide a proximal section with greater torquability and less flexibility, which transition to a more flexible distal section with greater flexibility to better maintain a bent shape when shaped by an operator. The positions and configurations of the proximal section, transition section, and distal section are tunable to optimize the benefits of effective torquability and shapeable tip performance.

Figure 6:
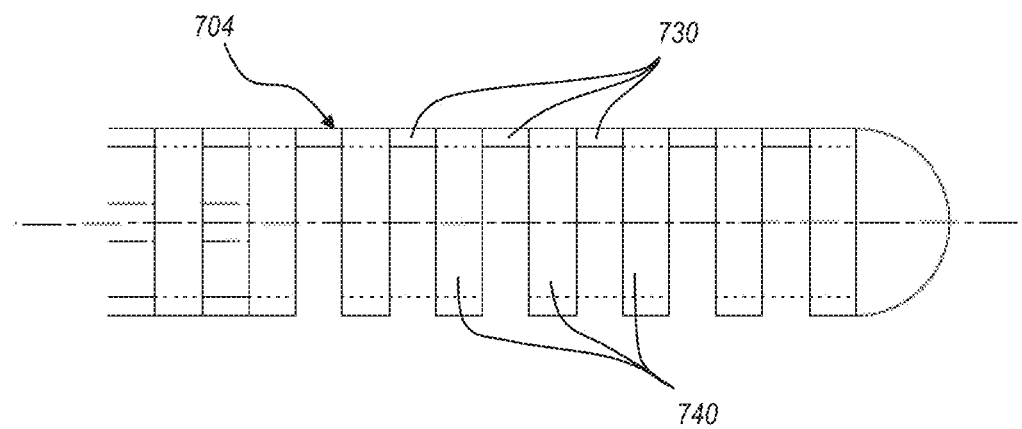
FIG. 6 illustrates an embodiment of a tube structure including a section having a one-sided one-beam cut pattern.

FIG. 6 illustrates another embodiment of a tube 704 having one-beam cuts forming a plurality of beams 730 and rings 740. As shown, the cuts are arranged so that the beams 730 are aligned along one side of the tube 704, rather than being alternatingly positioned by 180 degrees or some other angular amount. Such an embodiment can beneficially provide preferential bending in one direction (e.g., toward the aligned beams 730) so that the associated recovery force back toward the axis of the tube is further minimized.

Figure 7:
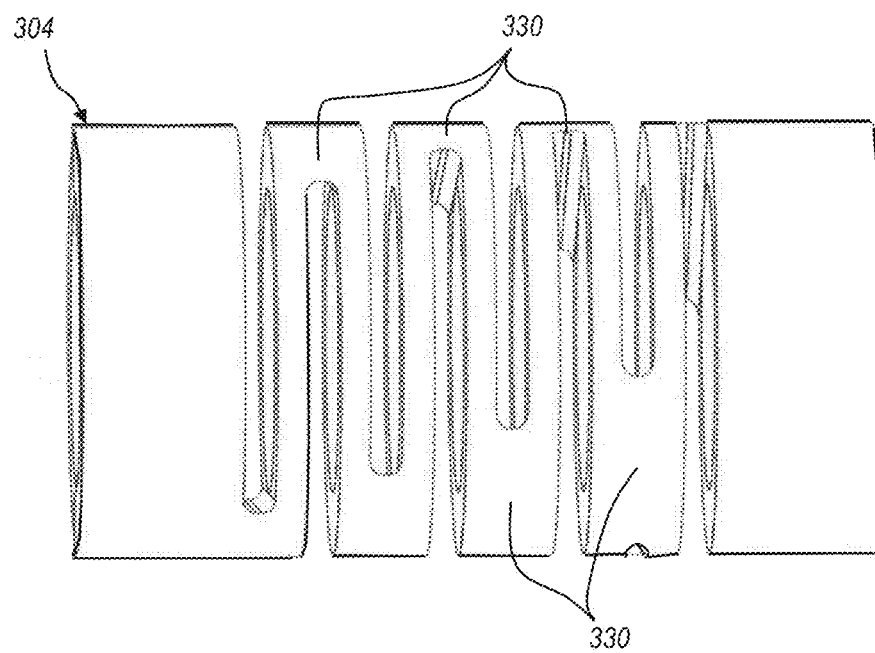
FIG. 7 illustrates an embodiment of a tube structure including a bypass cut pattern with an exemplary angular offset providing a helical pattern of resulting beams.

FIG. 7 illustrates an embodiment of a tube 304 having a bypass cut pattern and an angular offset between sets of cuts. As shown, the angular offset positions resulting beams 330 in a rotating/helical circumferential pattern along the length of the tube section. In some embodiments, a first angular offset is applied from one cut to the next within a set of cuts, and a second angular offset is applied from one set of cuts to the next set of cuts. For example, as illustrated in FIG. 7, each cut 308 in a pair of adjacent cuts may be offset by about 180 degrees so as to leave resultant beams 330 on opposite sides of one another with respect to the longitudinal axis of the guidewire, while each pair is offset from an adjacent pair by some other angular offset (e.g., by about 5 degrees in the illustrated embodiment). In this manner, the intra-set angular offset can position beams 330 on opposite sides of the guidewire axis, while the inter-set angular offset can adjust the angular position of successive beams enough to minimize preferred bending directions of the guidewire over a length of several sets of cuts 308.

Rotational offsets may also be applied to the cut patterns illustrated in FIGS. 3 through 6. In preferred embodiments, each successive cut or sets of cuts (e.g., every second cut, third, fourth, etc.) along the length of a given section is rotationally offset by about 1, 2, 3, 5, or 10 degrees, or is offset by about 1, 2, 3, 5, or 10 degrees off from 90 degrees in a two-beam configuration or 1, 2, 3, 5, or 10 degrees off from 180 degrees in a one-beam configuration. These rotational offset values have beneficially shown good ability to eliminate flexing bias.

For example, in a two-beam cutting pattern where each pair of beams are equally circumferentially spaced such as shown in FIG. 5, a rotational offset that is about 1, 2, 3, 5, or 10 degrees off from 90 degrees positions every other pair of beams along the length of the cut section with a misalignment of a few degrees. For example, a second pair of beams may be rotationally offset from a first pair of beams by slightly more or less than 90 degrees, but a third pair of beams will only be rotationally offset from the first pair by a few degrees, and a fourth pair of beams will only be rotationally offset from the second pair by a few degrees. When several successive pairs of beams are arranged this way along the length of a cut section of the guidewire device, the resulting structure allows the cut pattern to enhance flexibility without introducing or aggravating any directional flexibility bias.

The separate components and features of the tube embodiments shown in FIGS. 3 through 7 may be combined to form different tube configurations. For example, some tubes may be configured so as to have a section of bypass (one-beam) cuts (as in FIGS. 3, 6, and/or 7) and a section of symmetrically spaced two-beam cuts (as in FIG. 5), optionally also having one or more depth-offset two-beam cuts (as in FIG. 4). For example, some tube embodiments may include a proximal section having a symmetrically spaced two-beam cut pattern which transitions to a distal section having a bypass cut arrangement.

The embodiments described herein can beneficially enable more proximal regions of the tube to transmit relatively more torque, while reducing the torquability of more distal sections of the tube to allow for tip shaping without overly sacrificing torquability. Accordingly, the features of a guidewire device may be tuned to a particular need or application to optimize the operational relationship between torqueability, flexibility, and tip shapeability.

In preferred embodiments, the shapeable distal section of the core has a stiffness that is able to withstand an expected bending force from the tube acting upon the distal section of the core after it has been shaped. In some embodiments, the shapeable distal section of the core is formed from a material or combination of materials providing a modulus of elasticity that is about 1.5 to 4 times greater, or about 2 to 3 times greater than the modulus of elasticity of the material(s) used to form the tube.

Figure 8:
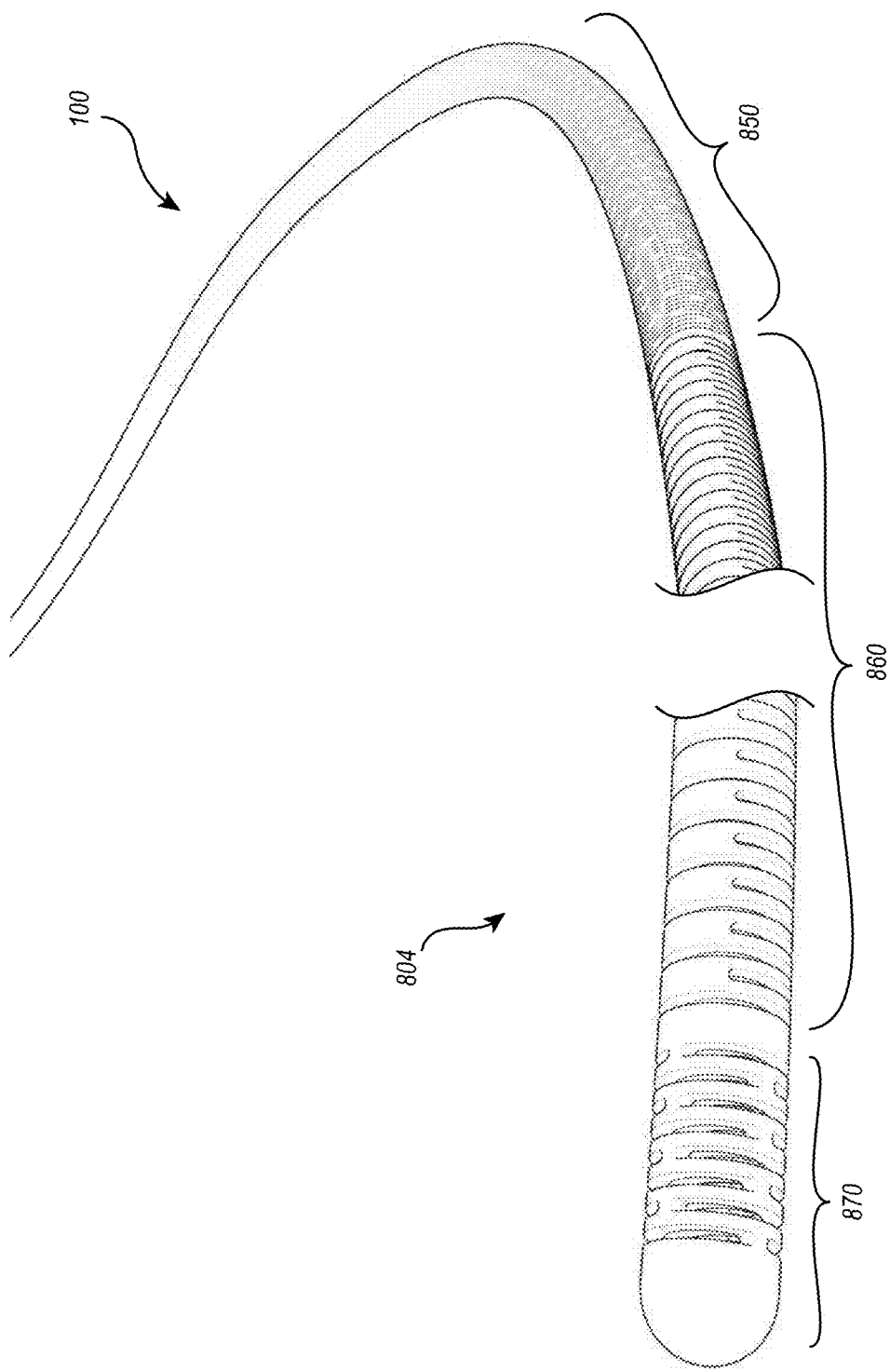
FIG. 8 illustrates a perspective view of an embodiment of a tube structure including three sections.

FIG. 8 illustrates an embodiment of a tube 804 having a first section 850, a second section 860, and a third section 870. The second section 860 is distal to the first section 850 and the third section 870 is distal to the second section 860. Each of the sections 850, 860, 870 may be distinguished from one another by the cutting pattern of each section. As discussed above with reference to other embodiments described herein, the cutting pattern may produce rings 840 and beams 803 within the tube. The sections 850, 860, 870 illustrated in FIG. 8 may have different cutting patterns in each section. For example, the first section 850 may have a two-beam cutting pattern, the second section 860 may have a one-beam cutting pattern, and the third section 870 may have a two-beam cutting pattern.

One will appreciate that other embodiments may include different cutting patterns from those illustrated in FIG. 8. For example, in one embodiment, the first section 850 may have a cutting pattern of greater than two beams, the second section 860 may have a two-beam cutting pattern or one-beam cutting pattern, and the third section 870 may have a one-beam cutting pattern or may be omitted. Also, other embodiments of the tube 804 may include more or less than three sections along the length thereof. For example, one embodiment of the tube 804 may include four or more sections. Also, for example, one embodiment of the tube 804 may include only one or two sections. Cut patterns shown in any of the other embodiments described herein may be utilized. Additional cut patterns and other features that may be utilized are also described in copending U.S. patent application Ser. No. 15/698,553, which is incorporated herein by this reference.

Figure 9A:
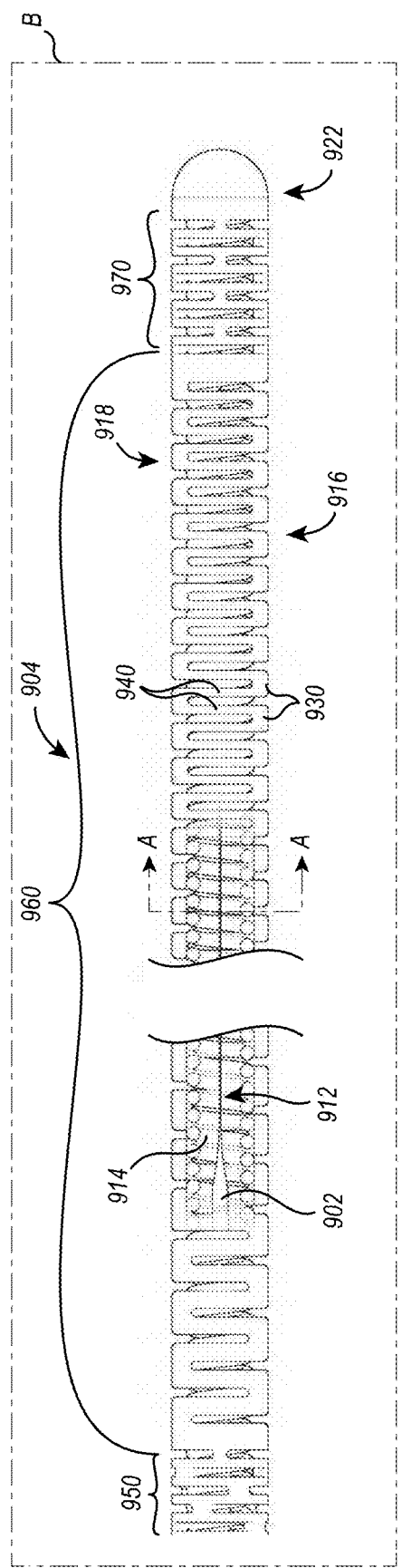
FIG. 9A illustrates a side view of an embodiment of a tube including a distal section of a core disposed therein.

FIG. 9A illustrates a side view of an embodiment of a tube 904 similar to the embodiment of the tube illustrated in FIG. 8. The tube of FIG. 9A also shows a partial cross-sectional view of the second section 960 to illustrate a distal section 912 of the core 902 extending through the tube 904 and the coil 914. Although only a partial cross-section is shown here, it will be understood that the core 902 will typically extend all the way to the distal end 922 of the device. In the illustrated embodiment, the second section 960 of the tube 904 includes a one-beam cutting pattern. The one-beam cutting pattern creates a series of axially extending beams 930 each disposed between a pair of adjacent circumferentially extending rings 940.

In the illustrated embodiment, successive beams 930 alternate in position from a first side 916 of the tube 904 to a second side 918 of the tube 904 (i.e., each successive beam 930 has a rotational offset of about 180°). In another embodiment, the beams 903 of the one-beam cutting pattern of the second section 960 may all be positioned along the same side of the tube to form a backbone of aligned beams 930 extending axially along the tube 904 and connecting the plurality of rings 940, similar to the embodiment shown in FIG. 6.

The one-beam cutting pattern of the second section 960, shown in FIG. 9A, forms a preferred bending plane B. The preferred bending plane B extends axially along the tube 904 and transversely across the tube 904, as indicated in FIG. 9A. Because the beams 930 of the second section 960 extend axially with the tube 904, the tube 904 is most flexible along the preferred bending plane B. That is, the beams 930 are configured such that the tube 904 is least resistant to being bent along the preferred bending plane B compared to any other planes. In this exemplary embodiment, the cutting pattern of the second section 960, whether producing an alternating pattern of beams 930 as shown in FIG. 9A or the single backbone of beams 930 as discussed above, produces a preferred bending plane B.

Figure 9B:
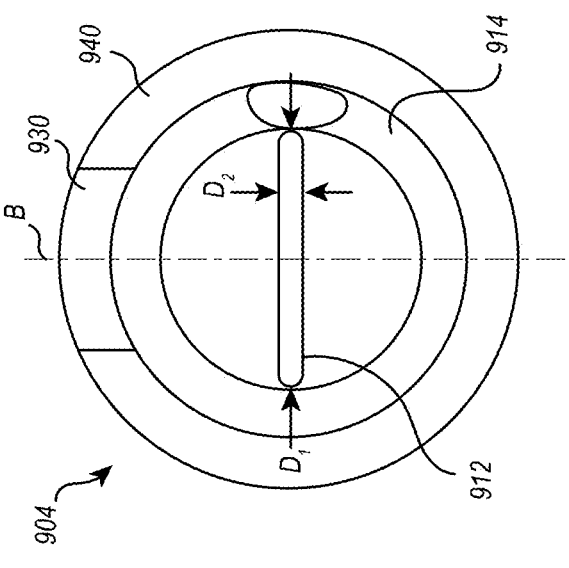
FIG. 9B illustrates a cross-sectional view of the tube of FIG. 9A.

Also, as shown in FIG. 9A, the distal section 912 of the core 902 tapers as it extends distally through the coil 914 and tube 904 and tapers at the distal portion into a flat, ribbon-like configuration. FIG. 9B illustrates a transverse cross-sectional view of the tube 904 through plane A-A of FIG. 9A. The distal section 912 of the core 902 is a substantially flat ribbon extending axially within at least the second section 960 of the tube 904. The ribbon configuration of the core 912 has a major dimension D1 and a minor dimension D2. The major dimension D1 of the distal section 912 of the core 902 is larger than the minor dimension D2 of the core 912 so that a major plane of the ribbon-like distal section 912 of the core 902 extends orthogonally (and preferably perpendicularly) to the preferred bending plane B. In this way, the distal section 912 of the core 902 is also least resistant to bending within the preferred bending plane B, along with the tube 904. In other words, the core 912 may taper to a ribbon-like configuration and extend axially along the tube 904 such that the distal section 912 of the core 902 is aligned with the beams 930 of the second section 960 so that it shares the preferred bending plane B with the tube 904.

In one embodiment, the second section 960 of the tube 904 is about 0.5 cm to about 5 cm in length. In another embodiment, the second section 960 of the tube 904 is about 1 cm to about 2 cm in length. In yet another embodiment, the second section 960 of the tube 904 is about 1 cm to about 1.5 cm in length. The distance from the distal end 922 to which the second section 960 extends may vary depending on the length of the tube 904 that is bent or shaped for a given procedure. These distances may vary between embodiments to accommodate various procedures, as necessary. Other features of the embodiments illustrated in FIGS. 8 through 9B, including materials and dimensions of the coil 914, tube 904, and core 902, and including particular features relating to the cutting patterns, may be similar to other embodiments described herein with reference to the other figures.

Figure 10:
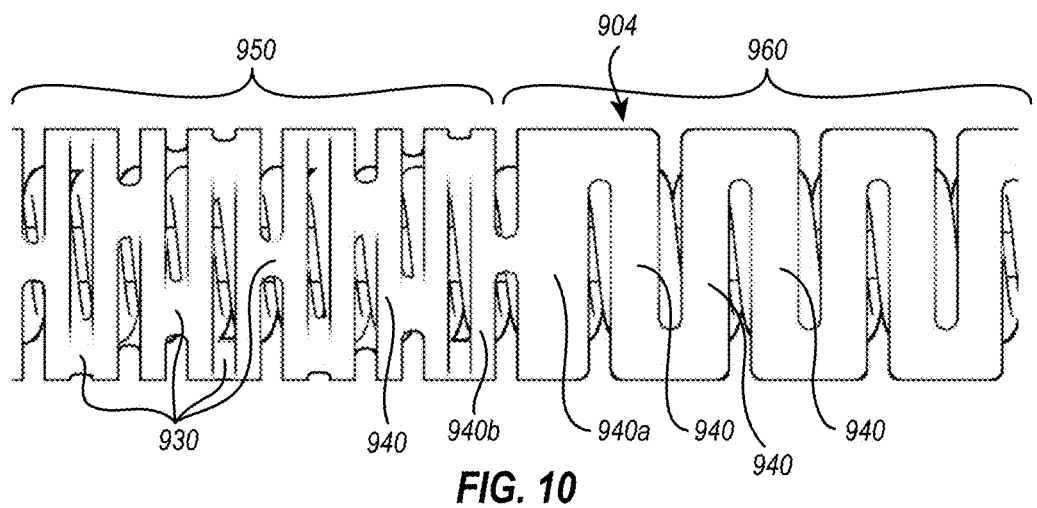
FIG. 10 illustrates an expanded side view of a transition between the first section and the second section of the tube of FIGS. 9A and 9B.

FIG. 10 illustrates a close-up view of a transition between the first section 950 and the second section 960 of the tube 904. In the illustrated embodiment, the first section 950 includes a two-beam cutting pattern and the second section 960 includes a one-beam cutting pattern. The stiffness of the tube 904 in each section depends, at least in part, on the amount of material remaining in the tube 904 once the cuts have been made and in the arrangement/spacing of the remaining beams 930. For example, a section of the tube 904 having two beams 930 between each pair of adjacent rings 940 will, all else being equal, have a greater stiffness than a section of the tube 904 having a single beam 930 of the same size between each pair of adjacent rings 940. Also, for example, a section of the tube 904 having a greater distance between cuts will, all else being equal, have a greater stiffness than a section with less distance between cuts. That is, the greater the distance between the cuts, the greater the thickness of the rings 940 formed between the cuts, and the greater the stiffness of the tube 904 in that section.

The cuts, rings 940, and beams 930 disposed at or near the transition point between the first section 950 and the second section 960 of the tube 904 illustrated in FIG. 10 are configured such that the stiffness profile of the tube 904 is approximately continuous across the transition between the two sections 950 and 960. In other words, the cutting patterns of the first and second sections 950 and 960 are arranged to avoid a significant jump up or down in stiffness from one side of the transition point to the other.

Of course, some level of discrete change in stiffness from measured segment to measured segment may be present depending on the particular level of granularity at which the stiffness is measured along the tube 904 and depending on the specified length of the measured segments. Because an infinite number of stiffness measurements cannot be made, a practically measurable stiffness profile will consist of measured stiffness levels at each of a series of discrete segment lengths of the tube. While jumps (i.e., change in stiffness) from one measured segment to the next measured segment may be discrete, the overall pattern of such jumps preferably approximates a linear series or at least a smooth curve. Thus, in the context of this disclosure, a "significant jump" occurs where a jump from one segment to the next is greater than either immediately adjacent jump by a factor of more than about 1.5. A significant jump is therefore avoided and the stiffness profile across the transition point is therefore "continuous" when no jump across the transition point is greater than either adjacent jump by a factor of more than about 1.5. Preferably no jump across the transition point is greater than either adjacent jump by a factor of more than about 1.2.

FIG. 10 illustrates an embodiment of the tube 904 having rings 940 and beams 930 that accomplish a continuous stiffness profile across the transition between sections 950, 960. In the illustrated embodiment, the axial thickness of the most proximal ring 940a of the second section 960 is greater than the axial thickness of the most distal ring 940b of the first section 95. In this way, the total amount of material of the tube 904 at the transition is similar between the sections 950, 960 at or near the transition. This results in a continuous stiffness across the transition, as described above. In addition, the axial thickness of the rings 940 of the second section 960 may decrease distally along the length of the tube 904 so that the stiffness correspondingly decreases. This is illustrated in FIG. 10 but shown more dramatically in FIG. 9A.

Figure 11:
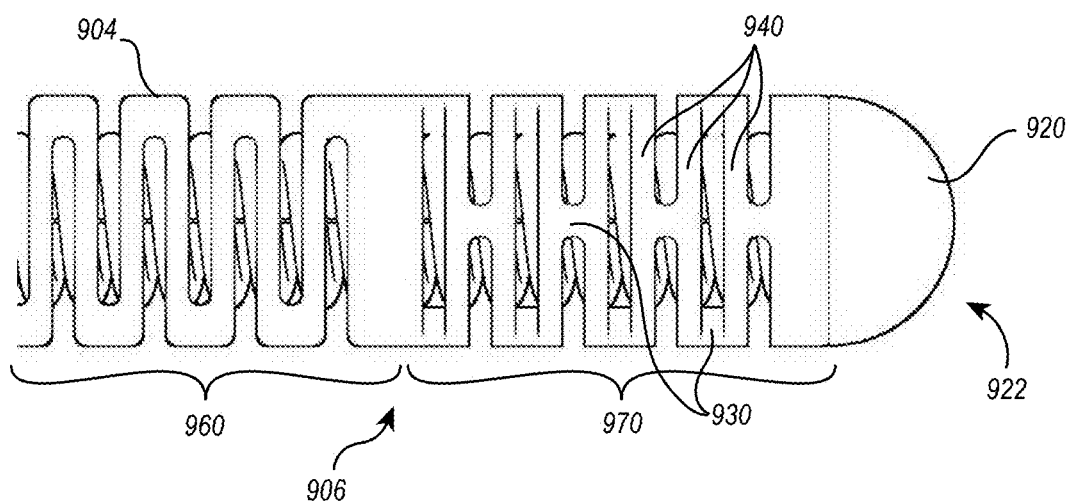
FIG. 11 illustrates an expanded side view of the distal tip of the tube of FIGS. 9A and 9B, including the second and third sections thereof.

Turning now to FIG. 11, the distal tip 906 of the tube 904 is shown. The distal tip 906 shown in FIG. 11 includes the third section 970, at least a portion of the second section 960, and a polymer adhesive 920 disposed distal to the third section 970 at the distal end 922 of the tube 904. The third section 970 of the tube 904 includes a two-beam cutting pattern forming two beams 930 between each pair of adjacent rings 940. This contrasts with the one-beam cutting pattern of the second section 960. One will appreciate that a transition between the second section 960 and the third section 970 may be similar to the transition between the first section 950 and the second section 960, as described above. That is, the stiffness of the tube 904 may be approximately continuous across the transition from the second section 960 to the third section 970.

The adhesive 920 disposed at the distal end 922 of the tube 904 may extend between the tube 904 and the core at the distal end 922 of the tube 904 to secure the tube 904 and core together. As illustrated in FIG. 1, the distal section 112 of the core 102 may extend distally beyond the tube 104 and into the adhesive 120. The adhesive 120 can thus function to couple the tube 104 to the core and/or coil 114.

Referring again to FIG. 11, the adhesive 920 may be disposed on the distal end 922 of the tube 904 and at least partially wick proximally and into one or more of the cuts between the various rings 940 and beams 930 of the third section 970. The two-beam cutting pattern of the third section 970 provides added surface area of the tube 904 material, compared to the one-beam cutting pattern of the second section 960, to which the adhesive 920 can bond. Thus, the two-beam cutting pattern of the third section 970 provides a stronger coupling between the adhesive 920 and distal section of the core and/or coil. One will appreciate that cutting patterns including more than two beams 930 between each pair of adjacent rings 940 may therefore serve to enhance the strength of the coupling between the tube 904 and the distal section of the core 102 and/or the coil. However, as discussed above, the more material the cuts remove from the tube 904, the less stiff the tube 904 will be, and vice versa.

Also, during manufacturing, disposing a larger amount of adhesive 920 on the distal end 922 of the tube 904 will result in the adhesive 920 wicking further proximally up the tube 904. The two-beam cutting pattern of the third section 970 provides an effective visual indicator to a manufacturer, due to the number and spacing of the cuts in the cutting pattern, in order to see how far proximally up the third section 970 the adhesive 920 wicks. This visual indication of the third section 970 may also assist a machine or other automated manufacturing device in detecting how far the adhesive 120 wicks proximally up the third section 970 during manufacturing.

For example, when a manufacturer disposes the adhesive 920 on the distal end 922 of the tube 904 during manufacturing, the adhesive may begin to wick through the spaces between the rings 940 and beams 930 in the third section 970. Because the two-beam cutting pattern of the third section 970 provides a visual indicator, in contrast to the one-beam cutting pattern of the second section 960, the manufacturer can more easily discern how far proximally up the tube 904 the adhesive wicks from one ring 940 to the next. The manufacturer can therefore determine how much adhesive 120 to dispose onto the distal end 922 of the tube 904. The manufacturer can also determine when to stop adding adhesive 120 based on a predetermined distance or ring 940 to which the adhesive 920 has wicked.

In one embodiment, the third section 970 of the tube 904 extends between about 0.5 mm and 1.5 mm from distal a distal end 922 of the tube 904. In another embodiment, the third section 970 of the tube 904 extends between about 0.75 mm and 1.25 mm from distal a distal end 922 of the tube 904. In yet another embodiment, the third section 970 of the tube 904 extends about 1 mm from distal a distal end 922 of the tube 904. The distance from the distal end 922 to which the third section 970 extends may vary depending on the length of the tube 904 that is needed to be bent or shaped, or the distance necessary for the adhesive 920 to wick sufficiently up the tube 904. These distances may vary between embodiments to accommodate various tubes and procedures, as necessary. Other features of the embodiments illustrated in FIGS. 10 and 11, including materials, properties, and dimensions of the coil 914, tube 904, and core 902, may be similar to other embodiments described herein with reference to the other figures.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a tube section of any of FIGS. 3 through 7 may be combined and used to form at least a portion of the tube of the guidewire device of FIGS. 1 and 2 or the guidewire devices of FIGS. 8 through 11. In addition, embodiments may include a tube having a plurality of bypass cuts, depth-offset two-beam cuts, and/or depth-symmetric two-beam cuts as described herein. In any of the foregoing combinations, the distal tip of the core wire may be rounded, flat, or another shape.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A guidewire device including a shapeable tip, the guidewire device comprising:
    a core including a proximal section and a distal section; and
    a shapeable tube structure coupled to the core such that the distal section of the core passes into the tube structure, the tube structure including a first section and a second section distal to the first section,
        wherein the tube structure includes a plurality of cuts extending transversely into the tube structure, each cut forming one or more beams defined by a remaining section of tube material, each beam connecting two adjacent rings of tube material,
        wherein the first section of the tube structure includes two or more beams between adjacent rings and the second section of the tube structure includes a single beam between adjacent rings,
        wherein a thickness of a most proximal ring of the second section is greater than a thickness of a most distal ring of the first section, and wherein a stiffness of the tube structure is continuous across a transition between the first and second sections.

2. The guidewire device of claim 1, wherein the second section includes an intermediate point, and wherein the rings of the second section proximal of the intermediate point have an average ring thickness that is greater than an average ring thickness of the rings of the second section distal of the intermediate point.

3. The guidewire device of claim 1, wherein the plurality of cuts of the second section are arranged with cuts of decreasing spacing toward a distal end of the tube structure.

4. The guidewire device of claim 1, wherein the second section is 0.5 cm to 5 cm in length.

5. The guidewire device of claim 1, wherein the second section is 1 cm to 2 cm in length.

6. The guidewire of claim 1, wherein the beams between rings in the second section alternate in position from a first side of the tube structure to a second side of the tube structure, the second side being opposite the first side by about 180 degrees.

7. The guidewire of claim 1, wherein the beams between rings in the second section are aligned on a single side of the tube structure to form a backbone of aligned beams connecting the plurality of rings within the second section.

8. The guidewire device of claim 1, further comprising a coil disposed within the tube structure so as to be positioned between an outer surface of the distal section of the core and an inner surface of the tube structure.

9. The guidewire device of claim 1, wherein the tube structure is formed from a superelastic material.

10. The guidewire device of claim 1, wherein the tube structure further comprises a third section distal to the second section, wherein the third section of the tube structure includes two or more beams between adjacent rings.

11. A guidewire device including a shapeable tip, the guidewire device comprising:
   a core including a proximal section and a distal section; and
   a tube structure coupled to the core such that the distal section of the core passes into the tube structure, the tube structure including a first section, a second section distal to the first section, and a third section distal to the second section,
      wherein the tube structure includes a plurality of cuts extending transversely into the tube structure, each cut forming one or more beams defined by a remaining section of tube material, each beam connecting two adjacent rings of tube material,
      wherein the first section of the tube structure includes two or more beams between each pair of adjacent rings,
      wherein the second section of the tube structure includes only a single beam between each pair of adjacent rings, and
      wherein the third section of the tube structure includes two or more beams between each pair of adjacent rings.

12. The guidewire device of claim 11, further comprising an adhesive disposed at the distal end of the tube structure that couples the tube structure to the core.

13. The guidewire device of claim 12, wherein the adhesive extends into the tube and between two or more rings in the third section of the tube structure.

14. The guidewire device of claim 11, wherein the second section is between about 0.5 cm and 5 cm in length.

15. The guidewire of claim 11, wherein the beams between rings in the second section alternate in position from a first side of the tube structure to a second side of the tube structure, the second side being opposite the first side by about 180 degrees.

16. The guidewire of claim 11, wherein the beams between rings in the second section are aligned on a single side of the tube structure to form a backbone of aligned beams connecting the plurality of rings within the second section.

17. The guidewire device of claim 11, further comprising a coil disposed within the tube structure so as to be positioned between an outer surface of the distal section of the core and an inner surface of the tube structure.

18. The guidewire device of claim 11, wherein the tube structure is formed from a superelastic material.

19. A guidewire device including a shapeable tip, the guidewire device comprising:
   a core including a proximal section and a distal section; and
   a shapeable tube structure coupled to the core such that the distal section of the core passes into the tube structure, the tube structure including a first section, a second section distal to the first section, and a third section distal to the second section,
      wherein the tube structure includes a plurality of cuts extending transversely into the tube structure, each cut forming one or more beams defined by a remaining section of tube material, each beam connecting two adjacent rings of tube material,
      wherein the first section of the tube structure includes two or more beams between adjacent rings, the second section of the tube structure includes a single beam between adjacent rings, and the third section includes two or more beams between adjacent rings,
   wherein a stiffness of the tube structure is continuous across a transition between the first and second sections, and
   wherein a thickness of a most proximal ring of the second section is greater than a thickness of a most distal ring of the first section.

* * * * *